United States Patent
Barz et al.

(10) Patent No.: US 12,419,965 B2
(45) Date of Patent: Sep. 23, 2025

(54) RNA PARTICLES COMPRISING POLYSARCOSINE

(71) Applicants: Johannes Gutenberg-Universität Mainz, Mainz (DE); BIONTECH SE, Mainz (DE)

(72) Inventors: Matthias Barz, Worms (DE); Benjamin Weber, Mainz (DE); Heinrich Haas, Mainz (DE); Philipp Heller, Mainz (DE); Sara Nogueira, Mainz (DE); Anne Schlegel, Mainz (DE)

(73) Assignees: BIONTECH SE, Mainz (DE); Johannes Gutenberg-Universität Mainz, Mainz (DE)

( * ) Notice: Subject to any disclaimer, the term of this patent is extended or adjusted under 35 U.S.C. 154(b) by 853 days.

(21) Appl. No.: 17/281,697

(22) PCT Filed: Sep. 30, 2019

(86) PCT No.: PCT/EP2019/076369
§ 371 (c)(1),
(2) Date: Mar. 31, 2021

(87) PCT Pub. No.: WO2020/070040
PCT Pub. Date: Apr. 9, 2020

(65) Prior Publication Data
US 2022/0001025 A1    Jan. 6, 2022

(51) Int. Cl.
*A61K 47/69* (2017.01)
*A61K 9/127* (2025.01)
(Continued)

(52) U.S. Cl.
CPC ........ *A61K 47/6935* (2017.08); *A61K 47/543* (2017.08); *A61K 47/6911* (2017.08);
(Continued)

(58) Field of Classification Search
CPC .............. A61K 47/6935; A61K 47/543; A61K 47/6911; A61K 48/0041; A61K 9/5146;
(Continued)

(56) References Cited

U.S. PATENT DOCUMENTS 5,614,505 A    3/1997  Gmeiner et al.
5,705,188 A    1/1998  Junichi et al.
(Continued)

FOREIGN PATENT DOCUMENTS

EP    2 942 348 A1    11/2015
WO    2009/046739 A1    4/2009
(Continued)

OTHER PUBLICATIONS

Weber, B.; Seidl, C.; Schwiertz, D.; Scherer, M.; Bleher, S.; Süss, R.; Barz, M. Polysarcosine-Based Lipids: From Lipopolypeptoid Micelles to Stealth-Like Lipids in Langmuir Blodgett Monolayers. Polymers 2016, 8, 427. https://doi.org/10.3390/polym8120427 (Year: 2016).*

(Continued)

*Primary Examiner* — Isaac Shomer
(74) *Attorney, Agent, or Firm* — McDonnell Boehnen Hulbert & Berghoff LLP

(57) ABSTRACT

The present disclosure relates to RNA particles for delivery of RNA to target tissues after administration, in particular after parenteral administration such as intravenous, intramuscular, subcutaneous or intratumoral administration, and compositions comprising such RNA particles. The RNA particles in one embodiment comprise single-stranded RNA such as mRNA which encodes a peptide or protein of interest, such as a pharmaceutically active peptide or protein. The RNA is taken up by cells of a target tissue and the RNA is translated into the encoded peptide or protein, which may exhibit its physiological activity.

11 Claims, 17 Drawing Sheets

(51) Int. Cl.
| | |
|---|---|
| A61K 47/54 | (2017.01) |
| A61K 48/00 | (2006.01) |
| C12N 15/85 | (2006.01) |
| C12N 15/88 | (2006.01) |
| A61K 9/51 | (2006.01) |
| A61K 47/18 | (2017.01) |
| A61K 47/24 | (2006.01) |
| A61K 47/28 | (2006.01) |

(52) U.S. Cl.
CPC .......... *A61K 48/0041* (2013.01); *C12N 15/85* (2013.01); *C12N 15/88* (2013.01); *A61K 9/127* (2013.01); *A61K 9/5146* (2013.01); *A61K 47/18* (2013.01); *A61K 47/24* (2013.01); *A61K 47/28* (2013.01)

(58) Field of Classification Search
CPC ........ A61K 47/18; A61K 47/24; A61K 47/28; A61K 47/62; A61K 47/6929; A61K 47/645; A61K 47/6939; A61K 48/0025; A61K 9/127; A61K 9/1272; C12N 15/85; C12N 15/88; C08G 69/10
See application file for complete search history.

(56) References Cited

U.S. PATENT DOCUMENTS

| | | | |
|---|---|---|---|
| 10,980,875 | B2 | 4/2021 | Pascolo et al. |
| 2006/0083780 | A1* | 4/2006 | Heyes ............... C12N 15/88 435/458 |
| 2008/0019908 | A1 | 1/2008 | Akitsu et al. |
| 2011/0123637 | A1 | 5/2011 | Pascolo et al. |
| 2012/0258046 | A1 | 10/2012 | Mutzke et al. |
| 2013/0189351 | A1* | 7/2013 | Geall ............... A61K 39/12 424/234.1 |
| 2015/0315541 | A1* | 11/2015 | Bancel ............... C07K 14/535 435/375 |
| 2018/0318436 | A1 | 11/2018 | Pascolo et al. |

FOREIGN PATENT DOCUMENTS

| | | |
|---|---|---|
| WO | 2009/088401 A2 | 7/2009 |
| WO | 2009/144230 A1 | 12/2009 |
| WO | 2011/005799 A2 | 1/2011 |
| WO | 2013/033438 A2 | 3/2013 |
| WO | WO 2013/185069 | 12/2013 |
| WO | 2016/072500 A1 | 5/2016 |
| WO | WO 2017/075531 | 5/2017 |
| WO | WO 2017/218704 | 12/2017 |
| WO | WO 2018/078053 | 5/2018 |
| WO | WO 2018/087753 | 5/2018 |
| WO | WO 2020/069718 | 4/2020 |
| WO | WO 2020/070040 | 4/2020 |
| WO | WO 2020/072605 | 4/2020 |

OTHER PUBLICATIONS

Van Tendeloo, Viggo FI, et al. "Highly efficient gene delivery by mRNA electroporation in human hematopoietic cells: superiority to lipofection and passive pulsing of mRNA and to electroporation of plasmid cDNA for tumor antigen loading of dendritic cells." (Year: 2001).*
Huesmann, David, et al. "A head-to-head comparison of poly (sarcosine) and poly (ethylene glycol) in peptidic, amphiphilic block copolymers." Polymer 67 (2015): 240-248. (Year: 2015).*
Hsu, Shu-Hao et al. "Cationic lipid nanoparticles for therapeutic delivery of siRNA and miRNA to murine liver tumor." Nanomedicine : nanotechnology, biology, and medicine vol. 9,8 (2013): 1169-80. doi:10.1016/j.nano.2013.05.007 (Year: 2013).*
Weber B, Seidl C, Schwiertz D, Scherer M, Bleher S, Suss R, Barz M. Polysarcosine-Based Lipids: From Lipopolypeptoid Micelles to Stealth-Like Lipids in Langmuir Blodgett Monolayers. Polymers (Basel). Dec. 9, 2016;8(12):427. doi: 10.3390/polym8120427. PMID: 30974703; PMCID: PMC6432249 (Year: 2016).*
Danaei et al., "Impact of Particle Size and Polydispersity Index on the Clinical Applications of Lipidic Nanocarrier Systems" Pharmaceutics 10(57):May 1-17, 2018 (Year: 2018).*
Diana D. Kang et al. "Engineering LNPs with polysarcosine lipids for mRNA delivery." Bioactive Materials, vol. 37, 2024, pp. 86-93. (Year: 2024).*
Alexander Birke, Jun Ling, and Matthias Barz. "Polysarcosine-containing copolymers: Synthesis, characterization, self-assembly, and applications." Progress in Polymer Science, vol. 81, 2018, pp. 163-208. (Year: 2018).*
David Huesmann et al. "A head-to-head comparison of poly(sarcosine) and poly(ethylene glycol) in peptidic, amphiphilic block copolymers." Polymer, vol. 67, 2015, pp. 240-248. (Year: 2015).*
King Hang Aaron Lau et al. "Surface-Grafted Polysarcosine as a Peptoid Antifouling Polymer Brush." Langmuir, vol. 28, 2012, pp. 16099-16107. (Year: 2012).*
Yali Hu et al. "Polysarcosine as an Alternative to PEG for Therapeutic Protein Conjugation." Bioconjugate Chemistry, vol. 29, 2018, pp. 2232-2238. (Year: 2018).*
Stefan Bleher et al. "Poly(Sarcosine) Surface Modification Imparts Stealth-Like Properties to Liposomes." vol. 15, Article 1904716, 2019, pp. 1-10. (Year: 2019).*
Benjamin Weber et al. "Polysarcosine-Based Lipids: From Lipopolypeptoid Micelles to Stealth-Like Lipids in Langmuir Blodgett Monolayers." vol. 8, 427, 2016, pp. 1-14. (Year: 2016).*
Wan et al: "Lipid nanoparticle delivery systems for siRNA-based therapeutics", Drug Delivery and Translational Research, Springer, Germany, vol. 4, No. 1, Jun. 28, 2013 (Jun. 28, 2013), pp. 74-83.
Belikov V. G., "Pharmaceutical Chemistry". 4th Edition, Moscow 2007, 6 pages; submitted with English translation.
Ichiki et al. Gan To Kagaku Ryoho, 1993, 20:2239-2242: Abstract.
Kaczmarek, J. C. et al., "Advances in the delivery of RNA therapeutics: from concept to clinical reality", Genome Medicine, 2017, 9, 60, pp. 2, 4-7.
Skold, Cancer Immunother., Aug. 15, 2015, 64: 1461-1473.
Kariko et al., "Phosphate-enhanced transfection of cationic lipid-complexed mRNA and plasmid DNA", Biochimica et Biophysica Acta, 1998, 320-334.
Schroeder et al., "Lipid-based nanotherapeutics for siRNA delivery", Journal of Internal Medicine, 2010, 267(1), 9-21.
Holm et al., "Synthesis and Characterization of Stimuli-Responsive Star-Like Polypept(o)ides: Introducing Biodegradable PeptoStars", Macromolecular Bioscience, 2017, 17(6), 14 pages.
Ahern, "Biochemical, Reagent Kits Offer Scientists Good Return on Investment" The Scientist, pp. 20-22, (Jul. 1995).
Barh et al., "MicroRNA let-7: an emerging next-generation cancer therapuetic," Curr. Oncol. 17(1):70-80 (Feb. 2010).
Bourquin et al., Systemic Cancer Therapy with a Small Molecule Agonist of Toll-like Receptor 7 Can Be Improved by Circumventing TLR Tolerance Cancer Res. 71:5123-33 (2011).
Diessner et al., Targeting of preexisting and induced breast cancer stem cells with trastuzumab and trastuzumab emantansine (T-DM1), Cell Death and Disease 5, e1149 (13 pages) (2014).
DeLong et al., "Characterization and performance of nucleic acid nanoparticles combined with protamine and gold" Biomaterials 30(32):6451-59 (Nov. 2009).
Jafari et al. "Nonviral Approach for targeted nucleic acid delivery," Current Medicinal Chemistry 19:197-208 (2012).
Kerkmann et al., "Immunostimulatory Properties of CpG-Oligonucleotides Are Enhanced by the Use of Protamine Nanoparticles" Oligonucleotides 16:313-22 (2006).
Makowska et al., "Sequential Induction of type I and II Interferons mediates a long-lasting gene induction in the liver in response to a novel toll-like receptor 9 agonist" Journal of Hepatology 48:743-49 (2013).
Mayer et al., "Oligonucleotide-prolamine-albumin nanoparticles: Prolamine sulfate causes drastic size reduction" Journal of Controlled Release, 106(1-2):181-87 (Aug. 2005).

(56) References Cited

OTHER PUBLICATIONS

Meyer et al., "Synthesis and biological evaluation of a bioresponsive and endosomolytic siRNA—polymer conjugate" Molecular Pharmaceuticals 6(3):752-62 (2009).
Nakamura et al., "A Double-modulation Strategy in Cancer Treatment With a Chemotherapeutic Agent and siRNA" Molecular Therapy, 19(11):2040-47 (Nov. 2011).
Plasay et al., "Selective cytotoxicity assay in anticancer drug of melittin isolated from bee venom (Apis cerana indica) to several human cell lines: HeLa, WiDR and Vero" Journal of Chemical and Pharmaceutical Sciences 9(4):2674-76 (Dec. 2016).
Rettig et al., "Particle Size and activation threshold:a new dimension of danger signaling" Blood 115(22):4533-41 (Jun. 2010).
Shima et al., "Synergistic Stimulation of Antigen Presenting Cells via TLR by Combining CpG ODN and Poly (y-glutamic acid)-Based Nanoparticles as Vaccine Adjuvants" Bioconjugate Chemistry 24:926-33 (2013).
Zhang et al., "Structural Analyses of Toll-like Receptor 7 Reveal Detailed RNA Sequence Specificity and Recognition Mechanism of Agonistic Ligands" Cell Reports 25:3371-81 (Dec. 2018).
Zhang et al., "Combinational delivery of c-myc siRNA and nucleoside analogs in a single, synthetic nanocarrier or targeted cancer therapy" Biomaterials 34(33):8459-68 (Nov. 2013).
The International Search Report (ISR) for PCT/EP2019/076369; dated Nov. 29, 2019, pp. 1-5.
The Written Opinion of the International Searching Authority for PCT/EP2019/076369; dated Nov. 29, 2019, pp. 1-7.
The International Search Report (ISR) for PCT/EP2016/075156; dated Jan. 9, 2017, pp. 1-4.
The Written Opinion of the International Searching Authority for PCT/EP2016/075156; dated Jan. 9, 2017, pp. 1-7.
The International Search Report (ISR) for PCT/EP2016/075146; dated Dec. 13, 2016, pp. 1-4.
The Written Opinion of the International Searching Authority for PCT/EP2016/075146; dated Dec. 13, 2016, pp. 1-5.
Parvanova et al., "The form of NY-ESO-1 antigen has an impact on the clinical efficacy of anti-tumor vaccination" Vaccine, 29:3832-36 (Apr. 2011).
Bleher et al., "Poly(sarcosine) surface modification imparts stealth-like properties to liposomes" Small 15(50): 1904716 (pp. 1-10) (Nov. 2019).
Hortz et al., "Cylindrical brush polymers with polysarcosine side chains: a novel biocompatible carrier for biomedical applications" Macromolecules 48(7):2074-86 (Mar. 2015).
Klein et al., "Efficient shielding of polyplexes using heterotelechelic polysarcosines" Polymers 10(6):689 (Jun. 2018).
Klinker et al., "Secondary-structure-driven self-assembly of reactive polypept(o)tides: controlling size, shape, and function of core cross-linked nanostructures" Angewandte Chemie Int Ed 56(32): 9608-13 (Jul. 2017).
Nogueira et al., "Polysarcosine-functionalized lipid nanoparticles for therapeutic mRNA delivery" ACS Appl. Nano Materials, 3(11):10614-65 (Nov. 2020).
Nogueira et al., "Polysarcosine-functionalized lipid nanoparticles for therapeutic mRNA delivery" ACS Appl. Nano Materials, 3(11):10614-65 (Nov. 2020). Supporting Information pp. S1-S13.
Ramishetti et al., "A combinatorial library of lipid nanoparticles for RNA delivery to leukocytes" Adv. Materials 32 (12):1906128 (pp. 1-8) (Mar. 2020).
Son et al., "Evasion of the accelerated blood clearance phenomenon by polysarcosine coating of liposomes" Journal of Controlled Release 322(17):209-16 (Mar. 2020).
Danaei et al., "Impact of Particle Size and Polydispersity Index on the Clinical Applications of Lipidic Nanocarrier Systems" Pharmaceutics 10(57):1-17 (May 2018).

* cited by examiner

RNA PARTICLES COMPRISING POLYSARCOSINE

CROSS-REFERENCE TO RELATED APPLICATIONS

This application is the US national phase under 35 U.S.C. § 371 of International Application No. PCT/EP2019/076369, filed on Sep. 30, 2019, which claims the benefit of International Application No. PCT/EP2018/076633, filed on Oct. 1, 2018 and International Application No. PCT/EP2019/069551, filed on Jul. 19, 2019, the contents of which are incorporated herein by reference in their entirety.

TECHNICAL FIELD

The present disclosure relates to RNA particles for delivery of RNA to target tissues after administration, in particular after parenteral administration such as intravenous, intramuscular, subcutaneous or intratumoral administration, and compositions comprising such RNA particles. The RNA particles in one embodiment comprise single-stranded RNA such as mRNA which encodes a peptide or protein of interest, such as a pharmaceutically active peptide or protein. The RNA is taken up by cells of a target tissue and the RNA is translated into the encoded peptide or protein, which may exhibit its physiological activity.

BACKGROUND

The use of RNA for delivery of foreign genetic information into target cells offers an attractive alternative to DNA. The advantages of using RNA include transient expression and a non-transforming character. RNA does not need to enter the nucleus in order to be expressed and moreover cannot integrate into the host genome, thereby eliminating the risk of oncogenesis.

RNA may be delivered to a subject using different delivery vehicles, mostly based on cationic polymers or lipids which together with the RNA form nanoparticles. The nanoparticles are intended to protect the RNA from degradation, enable delivery of the RNA to the target site and facilitate cellular uptake and processing by the target cells. For delivery efficacy, in addition to the molecular composition, parameters like particle size, charge, or grafting with molecular moieties, such as polyethylene glycol (PEG) or ligands, play a role. Grafting with PEG is considered to reduce serum interactions, to increase serum stability and to increase circulation time, which can be helpful for certain targeting approaches. Ligands which bind to receptors at the target site can help to improve targeting efficacy. Furthermore, PEGylation can be used for particle engineering. For example, if Lipid Nanoparticles (LNP) are manufactured by mixing an aqueous phase of the RNA with an organic phase of the lipids a certain fraction of PEG-conjugated lipid in the lipid mixture is required, otherwise the particles aggregate during the mixing step. It has been shown that by variation of the molar fraction of PEG-lipids comprising PEG at different molar masses the size of the particles can be adjusted. As well, the particle size may be adjusted by variation of the molar mass of the PEG moiety of the PEGylated lipids. Typical sizes which are accessible are in the range between 30 and 200 nm (Belliveau et al, 2012, Molecular Therapy-Nucleic Acids 1, e37). So-formed particles have additionally the advantage, that, due to the PEG fraction, they interact less with serum components, and have a longer circulation half-life, which is desirable in many drug delivery approaches. Without PEG-lipids, no particles with discrete size can be formed; the particles form large aggregates and precipitate.

So, for techniques where LNPs are formed from an ethanolic and an aqueous phase, one of the primary roles of PEG-lipids is to facilitate particle self-assembly by providing a steric barrier at the surface of nascent particles formed when nucleic acids are rapidly mixed in ethanol solutions containing lipids to bind the RNA. PEG steric hindrance prevents inter-particle fusion and promotes the formation of a homogeneous population of LNPs with diameters <100 nm.

PEG is the most widely used and gold standard "stealth" polymer in drug delivery. PEG-lipids are typically incorporated into systems to prepare a homogenous and colloidally stable nanoparticle population due to its hydrophilic steric hindrance property (PEG shell prevents electrostatic or Van der Waals attraction that leads to aggregation). PEGylation enables to attract a water shell around the polymer shielding the RNA complex from opsonization with serum proteins, increasing serum half-life as well as reducing rapid renal clearance which results in an improvement of the pharmacokinetic behavior. Variation of the length of the acyl chains (C18, C16 or C14) of the lipids modifies the stability of the incorporation of the PEG-lipid in the particles which leads to a modulation of the pharmacokinetics. The use of a PEG-lipid containing short (C14) acyl chains that dissociates from LNPs in vivo with a halftime <30 min results in optimum hepatocyte gene-silencing potency (Chen et al, 2014, J Control Release 196:106-12; Ambegia et al., 2005, Biochimica et Biophysica Acta 1669:155-163). In addition, tight control of particle size can be obtained by varying the PEG-lipid parameter: higher PEG MW or higher molar fraction of PEG-lipids in the particles lead to smaller particles.

Despite these advantages, PEGylation of nanoparticles may lead as well to several effects which are detrimental to the intended use for drug delivery. PEGylation of liposomes and LNPs is known to reduce the cellular uptake and endosomal escape, thus reducing at the end the overall transfection efficiency. Indeed, the PEG shell provides a steric barrier to efficient binding of particles to the cell and also hinders endosomal release by preventing membrane fusion between the liposome and the endosomal membrane. This is why the type of PEG-lipid and the amount of PEG-lipid used must be always carefully adjusted. It should provide sufficient stealth effect for in vivo and stabilization aspects on the one hand, while not hindering transfection on the other. This phenomenon is known as the "PEG Dilemma".

Besides lowering transfection efficiency, PEGylation has been associated with accelerated blood clearance (ABC) phenomenon induced by anti-PEG antibodies and/or complement activation as well as storage diseases (Bendele A et al., 1998, Toxicolocical Sciences 42, 152-157; Young M A et al., 2007, Translational Research 149(6), 333-342; S. M. Moghimi, J. Szebeni, 2003, Progress in Lipid Research 42:463-478). Ishida et al and Laverman et al reported that intravenous injection in rats of PEG-grafted liposomes may significantly alter the pharmacokinetic behavior of a second dose when this second dose is administered after an interval of several days (Laverman P et al., 2001, J Pharmacol Exp Ther. 298(2), 607-12; Ishida et al., 2006, J Control Release 115(3), 251-8). The phenomenon of "accelerated blood clearance" (ABC) appears to be inversely related to the PEG content of liposomes. The presence of anti-PEG antibodies in the plasma induces a higher clearance of the particles by the Monophagocyte System (MPS) which at the end reduces the efficacy of the drug.

PEG is also supposed to induce complement activation, which can lead to hypersensitivity reaction, also known as Complement-Activation Related Pseudo-Allergy (CARPA). It is still not clear from the literature if the activation of complement is due to the nanoparticle in general or to the presence of PEG in particular.

The presence of PEG in lipidic nanoparticles may also induce a specific immune response. Semple et al. reported that liposomes containing PEG-lipid derivatives and encapsulated antisense oligodeoxynucleotide or plasmid DNA elicit a strong immune response that results in the rapid blood clearance of subsequent doses in mice. The magnitude of this response was sufficient to induce significant morbidity and, in some instances, mortality. Rapid elimination of liposome-encapsulated ODN from blood depended on the presence of PEG-lipid in the membrane because the use of non-pegylated liposomes or liposomes containing rapidly exchangeable PEG-lipid abrogated the response. The generation of anti-PEG antibody and the putative complement activation were a likely explanation for the rapid elimination of the vesicles from the blood. (Semple et al., 2005, J Pharmacol Exp Ther. 312(3), 1020-6).

As PEG may induce immune responses there is a need to avoid it for certain applications where multiple injections are needed. Examples are therapies using mRNA, for example for protein replacement therapy. Here, the risk can be particularly high due to the potential intrinsic immunogenicity of RNA.

Thus, there remains a need in the art for efficient methods and compositions for introducing RNA into cells which avoid the disadvantages accompanied by use of PEG. The present disclosure addresses these and other needs.

The inventors surprisingly found that the RNA particle formulations described herein fulfill the above mentioned requirements. In particular it is demonstrated that polysarcosine-lipid conjugates are suitable components for assembly of RNA nanoparticles. Polysarcosine is composed of repeated units of the natural amino acid sarcosine (N-methylglycine) and is biodegradable. Polysarcosine-lipid conjugates enable manufacturing of RNA nanoparticles with different techniques, resulting in defined surface properties and controlled size ranges. Manufacturing can be done by robust processes, compliant with the requirements for pharmaceutical manufacturing. The particles can be end-group functionalized with different moieties to modulate charge or to introduce specific molecular moieties like ligands.

SUMMARY

In one aspect, the invention relates to a composition comprising a plurality of RNA particles, wherein each particle comprises:
(i) RNA;
and
(ii) one or more components which associate with RNA to form RNA particles,
wherein polysarcosine is conjugated to at least one of the one or more components.

In one embodiment, the RNA particles are non-viral RNA particles. In one embodiment, the one or more components which associate with RNA to form particles comprise one or more polymers. In one embodiment, the one or more polymers comprise a cationic polymer. In one embodiment, the cationic polymer is an amine-containing polymer. In one embodiment, the one or more polymers comprise one or more polymers selected from the group consisting of poly-L-lysine, polyamidoamine, polyethyleneimine, chitosan and poly(β-amino esters).

In one embodiment, the one or more components which associate with RNA to form particles comprise one or more lipids or lipid-like materials. In one embodiment, the one or more lipids or lipid-like materials comprise a cationic or cationically ionizable lipid or lipid-like material. In one embodiment, the cationically ionizable lipid or lipid-like material is positively charged only at acidic pH and does not remain cationic at physiological pH. In one embodiment, the one or more lipids or lipid-like materials comprise one or more additional lipids or lipid-like materials. In one embodiment, the polysarcosine is conjugated to at least one of the one or more additional lipids or lipid-like materials.

In a further aspect, the invention relates to a composition comprising a plurality of RNA-lipid particles, wherein each particle comprises:
(a) RNA;
(b) a cationic or cationically ionizable lipid or lipid-like material;
and
(c) a polysarcosine-lipid conjugate or a conjugate of polysarcosine and a lipid-like material.

In one embodiment, each particle further comprises:
(d) a non-cationic lipid or lipid-like material.

In one embodiment, the cationic or cationically ionizable lipid or lipid-like material comprises from about 20 mol % to about 80 mol % of the total lipid and lipid-like material present in the particles.

In one embodiment, the non-cationic lipid or lipid-like material comprises from about 0 mol % to about 80 mol % of the total lipid and lipid-like material present in the particles.

In one embodiment, the polysarcosine-lipid conjugate or conjugate of polysarcosine and a lipid-like material comprises from about 0.25 mol % to about 50 mol % of the total lipid and lipid-like material present in the particles.

In one embodiment, the non-cationic lipid or lipid-like material comprises a phospholipid. In one embodiment, the non-cationic lipid or lipid-like material comprises cholesterol or a cholesterol derivative. In one embodiment, the non-cationic lipid or lipid-like material comprises a mixture of a phospholipid and cholesterol or a cholesterol derivative. In one embodiment, the phospholipid is selected from the group consisting of distearoylphosphatidylcholine (DSPC), dipalmitoylphosphatidylcholine (DPPC), or a mixture thereof. In one embodiment, the non-cationic lipid or lipid-like material comprises a mixture of DSPC and cholesterol.

In one embodiment, the polysarcosine-lipid conjugate or a conjugate of polysarcosine and a lipid-like material comprises the following general formula (I):

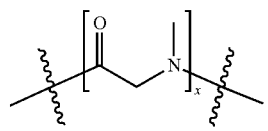

In one embodiment, the polysarcosine-lipid conjugate or a conjugate of polysarcosine and a lipid-like material comprises the following general formula (II):

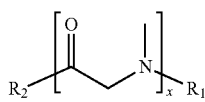

wherein one of $R_1$ and $R_2$ comprises a hydrophobic group and the other is H, a hydrophilic group or a functional group optionally comprising a targeting moiety.

In one embodiment, the polysarcosine-lipid conjugate or a conjugate of polysarcosine and a lipid-like material comprises the following general formula (III):

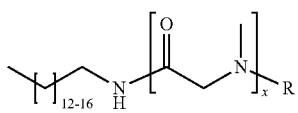

wherein R is H, a hydrophilic group or a functional group optionally comprising a targeting moiety.

In one embodiment of all aspects of the invention, the particles do not comprise a polyethyleneglycol-lipid conjugate or a conjugate of polyethyleneglycol and a lipid-like material, and preferably do not comprise polyethyleneglycol.

In one embodiment of all aspects of the invention, the RNA is mRNA.

In one embodiment of all aspects of the invention, the cationic or cationically ionizable lipid or lipid-like material comprises N,N-dimethyl-2,3-dioleyloxy)propylamine (DODMA), N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-KC2-DMA), 2,2-dilinoleyl-4-dimethylaminomethyl-[1,3]-dioxolane (DLin-K-DMA), or a mixture thereof.

In one embodiment of all aspects of the invention, the polysarcosine comprises between 2 and 200 sarcosine units.

In one embodiment of all aspects of the invention, the polysarcosine-lipid conjugate or a conjugate of polysarcosine and a lipid-like material is a member selected from the group consisting of a polysarcosine-diacylglycerol conjugate, a polysarcosine-dialkyloxypropyl conjugate, a polysarcosine-phospholipid conjugate, a polysarcosine-ceramide conjugate, and a mixture thereof.

In one embodiment of all aspects of the invention, the particles are nanoparticles.

In one embodiment of all aspects of the invention, the particles comprise a nanostructured core.

In one embodiment of all aspects of the invention, the particles have a size of from about 30 nm to about 500 nm.

In one embodiment of all aspects of the invention, the polysarcosine-conjugate inhibits aggregation of the particles.

In a further aspect, the invention relates to a method for delivering RNA to cells of a subject, the method comprising administering to a subject a composition described herein.

In a further aspect, the invention relates to a method for delivering a therapeutic peptide or protein to a subject, the method comprising administering to a subject a composition described herein, wherein the RNA encodes the therapeutic peptide or protein.

In a further aspect, the invention relates to a method for treating or preventing a disease or disorder in a subject, the method comprising administering to a subject a composition described herein, wherein delivering the RNA to cells of the subject is beneficial in treating or preventing the disease or disorder.

In a further aspect, the invention relates to a method for treating or preventing a disease or disorder in a subject, the method comprising administering to a subject a composition described herein, wherein the RNA encodes a therapeutic peptide or protein and wherein delivering the therapeutic peptide or protein to the subject is beneficial in treating or preventing the disease or disorder.

In one embodiment, the subject is a mammal. In one embodiment, the mammal is a human.

BRIEF DESCRIPTION OF THE DRAWINGS

FIG. 4: Influence of different polysarcosine end groups on particle size and zeta potential. PSarc consisting of 20 repeat units with either an amine group, a carboxylated or an acetylated end group were tested in direct comparison. All other formulation parameters were maintained constant. Formation of LNPs with all tested end groups was successful, where the correlation between PSarc fraction and particle characteristics (size and zeta potential) was similar.

DETAILED DESCRIPTION

Figure 1:
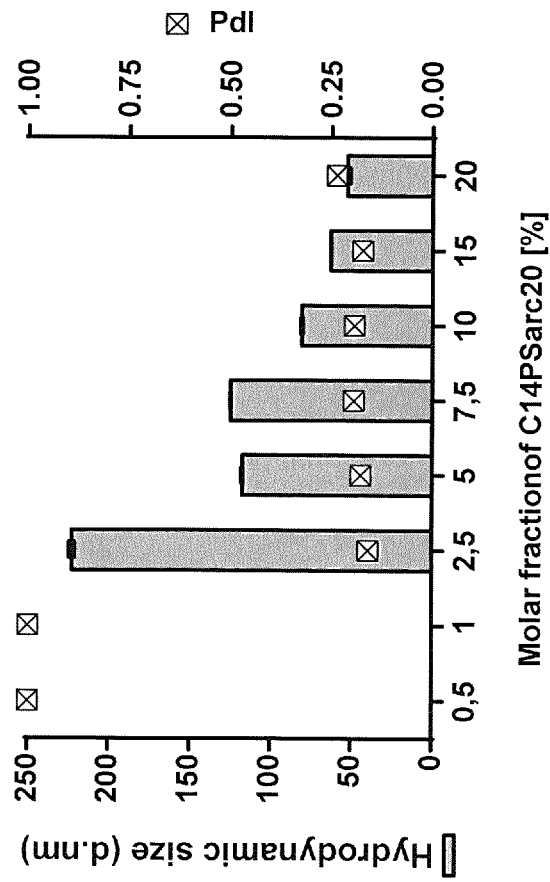
FIG. 1: Relationship between the particle size and the molar fraction of pSarcosylated LNPs. Lipid nanoparticles were manufactured using lipid mixtures comprising increasing molar fractions of C14PSarc20. Under suitable conditions, colloidally stable particles can be obtained. While with very low fractions of PSarc (0.5 and 1%) no particles of measurable size were formed, at 2.5 mol % and above particles with discrete size and low polydispersity index were obtained. The particle size could be accurately fine-tuned by variation of the PSarc fraction. Particle size decreased monotonously from about 200-250 nm with 2.5 mol % of PSarc to about 50 nm with 20 mol % of PSarc.

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or +3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e. for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

Terms such as "reduce" or "inhibit" as used herein means the ability to cause an overall decrease, for example, of about 5% or greater, about 10% or greater, about 20% or greater, about 50% or greater, or about 75% or greater, in the level. The term "inhibit" or similar phrases includes a complete or essentially complete inhibition, i.e. a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

"Physiological pH" as used herein refers to a pH of about 7.4.

As used in the present disclosure, "% w/v" refers to weight by volume percent, which is a unit of concentration measuring the amount of solute in grams (g) expressed as a percent of the total volume of solution in milliliters (mL).

As used in the present disclosure, "mol %" is defined as the ratio of the number of moles of one component to the total number of moles of all components, multiplied by 100.

The term "ionic strength" refers to the mathematical relationship between the number of different kinds of ionic species in a particular solution and their respective charges. Thus, ionic strength I is represented mathematically by the formula $$I = \frac{1}{2} \cdot \sum_i z_i^2 \cdot c_i$$

in which c is the molar concentration of a particular ionic species and z the absolute value of its charge. The sum $\Sigma$ is taken over all the different kinds of ions (i) in solution.

According to the disclosure, the term "ionic strength" in one embodiment relates to the presence of monovalent ions. Regarding the presence of divalent ions, in particular divalent cations, their concentration or effective concentration (presence of free ions) due to the presence of chelating agents is in one embodiment sufficiently low so as to prevent degradation of the RNA. In one embodiment, the concentration or effective concentration of divalent ions is below the catalytic level for hydrolysis of the phosphodiester bonds between RNA nucleotides. In one embodiment, the concentration of free divalent ions is 20 μM or less. In one embodiment, there are no or essentially no free divalent ions.

"Osmolality" refers to the concentration of solutes expressed as the number of osmoles of solute per kilogram of solvent.

The term "freezing" relates to the phase transition from the liquid to the solid state. It usually occurs on lowering the temperature of a system below a critical temperature and is accompanied by a characteristic change of enthalpy of the system.

The term "lyophilizing" or "lyophilization" refers to the freeze-drying of a substance by freezing it and then reducing the surrounding pressure to allow the frozen medium in the substance to sublimate directly from the solid phase to the gas phase.

The term "spray-drying" refers to spray-drying a substance by mixing (heated) gas with a fluid that is atomized (sprayed) within a vessel (spray dryer), where the solvent from the formed droplets evaporates, leading to a dry powder.

The term "cryoprotectant" relates to a substance that is added to a formulation in order to protect the active ingredients during the freezing stages.

The term "lyoprotectant" relates to a substance that is added to a formulation in order to protect the active ingredients during the drying stages.

The term "reconstitute" relates to adding a solvent such as water to a dried product to return it to a liquid state such as its original liquid state.

The term "recombinant" in the context of the present disclosure means "made through genetic engineering". In one embodiment, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

In the context of the present disclosure, the term "particle" relates to a structured entity formed by molecules or molecule complexes. In one embodiment, the term "particle" relates to a micro- or nano-sized structure, such as a micro- or nano-sized compact structure dispersed in a medium.

In the context of the present disclosure, the term "RNA particle" relates to a particle that contains RNA. Electrostatic interactions between positively charged molecules such as polymers and lipids and negatively charged RNA are involved in particle formation. This results in complexation and spontaneous formation of RNA particles. In one embodiment, a RNA particle is a nanoparticle.

As used in the present disclosure, "nanoparticle" refers to a particle having an average diameter suitable for intravenous administration.

The term "average diameter" refers to the mean hydrodynamic diameter of particles as measured by dynamic laser light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

Generally, the RNA-lipid particles described herein are obtainable by mixing an RNA containing phase with a lipid containing phase. This can be mixing an ethanol phase or other water-miscible solvent comprising lipids, such as cationic lipids like DODMA, and additional lipids, with an aqueous phase comprising RNA. Another option is mixing an aqueous phase comprising the lipids, for example comprising lipids in form of liposomes or other types of lipid dispersions, with another aqueous phase comprising RNA.

RNA-Containing Particles

Different types of RNA containing particles have been described previously to be suitable for delivery of RNA in particulate form (e.g. Kaczmarek, J. C. et al., 2017, Genome Medicine 9, 60). For non-viral RNA delivery vehicles, nanoparticle encapsulation of RNA physically protects RNA from degradation and, depending on the specific chemistry, can aid in cellular uptake and endosomal escape.

The present disclosure describes particles comprising RNA and one or more components which associate with RNA to form RNA particles and compositions comprising such particles. The RNA particles may comprise RNA which is complexed in different forms by non-covalent interactions to the particle. The particles described herein are not viral particles, in particular infectious viral particles, i.e., they are not able to virally infect cells. The RNA-containing particles may be, for example, in the form of proteinaceous particles, in the form of polymer-comprising particles or in the form of lipid-containing particles. Suitable proteins, polymers or lipids are included by the term "particle forming components" or "particle forming agents". The term "particle forming components" or "particle forming agents" relates to any components which associate with RNA to form RNA particles. Such components include any component which can be part of RNA particles.

Proteins, polymers, lipids as well as other hydrophilic, hydrophobic or amphiphilic compounds are typical constituents of RNA particle formulations.

Given their high degree of chemical flexibility, polymers are commonly used materials for nanoparticle-based delivery. Typically, cationic polymers are used to electrostatically condense the negatively charged RNA into nanoparticles. These positively charged groups often consist of amines that change their state of protonation in the pH range between 5.5 and 7.5, thought to lead to an ion imbalance that results in endosomal rupture. Polymers such as poly-L-lysine, polyamidoamine, protamine and polyethyleneimine, as well as naturally occurring polymers such as chitosan have all been applied to RNA delivery. In addition, some investigators have synthesized polymers specifically for nucleic acid delivery. Poly(Q-amino esters), in particular, have gained widespread use in nucleic acid delivery owing to their ease of synthesis and biodegradability.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties such as those described herein.

If more than one type of repeat unit is present within the polymer, then the polymer is said to be a "copolymer." It is to be understood that in any embodiment employing a polymer, the polymer being employed can be a copolymer in some cases. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body.

In certain embodiments, the particle forming polymer may be protamine or polyalkyleneimine such as polyethyleneimine.

The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the disclosure, the term "protamine" as used herein is meant to comprise any protamine amino acid sequence obtained or derived from natural or biological sources including fragments thereof and multimeric forms of said amino acid sequence or fragment thereof as well as (synthesized) polypeptides which are artificial and specifically designed for specific purposes and cannot be isolated from native or biological sources.

In one embodiment, the polyalkyleneimine comprises polyethylenimine and/or polypropylenimine, preferably polyethyleneimine. A preferred polyalkyleneimine is polyethyleneimine (PEI). The average molecular weight of PEI is preferably $0.75 \cdot 10^2$ to $10^7$ Da, preferably 1000 to $10^5$ Da, more preferably 10000 to 40000 Da, more preferably 15000 to 30000 Da, even more preferably 20000 to 25000 Da.

Preferred according to the disclosure is linear polyalkyleneimine such as linear polyethyleneimine (PEI).

Lipid-Containing Particles

In one embodiment, the RNA particles described herein comprise at least one lipid or lipid-like material as particle forming agent. Lipid carriers contemplated for use herein include any substances with which RNA can be associated, e.g. by forming complexes with the RNA or forming vesicles in which the RNA is enclosed or encapsulated.

The terms "lipid" and "lipid-like material" are broadly defined herein as molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually poorly soluble in water. In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). The hydrophilic groups may comprise polar and/or charged groups and include carbohydrates, phosphate, carboxylic, sulfate, amino, sulfhydryl, nitro, hydroxyl, and other like groups.

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as sterol-containing metabolites such as cholesterol.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides.

Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

The glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-

Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

According to the disclosure, lipids and lipid-like materials may be cationic, anionic or neutral. Neutral lipids or lipid-like materials exist in an uncharged or neutral zwitterionic form at a selected pH.

Preferably, RNA particles described herein comprise a cationic or cationically ionizable lipid or lipid-like material. Cationic or cationically ionizable lipids and lipid-like materials may be used to electrostatically bind RNA. Cationically ionizable lipids and lipid-like materials are materials that are preferably positively charged only at acidic pH. This ionizable behavior is thought to enhance efficacy through helping with endosomal escape and reducing toxicity as compared with particles that remain cationic at physiological pH. The particles may also comprise non-cationic lipids or lipid-like materials. Collectively, anionic and neutral lipids or lipid-like materials are referred to herein as non-cationic lipids or lipid-like materials. Optimizing the formulation of RNA particles by addition of other hydrophobic moieties, such as cholesterol and lipids, in addition to an ionizable/cationic lipid or lipid-like material enhances particle stability and can significantly enhance efficacy of RNA delivery.

In one embodiment, the cationic or cationically ionizable lipid or lipid-like material comprises a head group which includes at least one nitrogen atom (N) which is positive charged or capable of being protonated.

Polysarcosine Conjugate

One or more of the particle-forming components described herein such as polymers, lipids or lipid-like materials used in the particles described herein comprise polysarcosine (poly(N-methylglycine)). The polysarcosine may comprise acetylated (neutral end group) or other functionalized end groups. In the case of RNA-lipid particles, the polysarcosine in one embodiment is conjugated to, preferably covalently bound to a non-cationic lipid or lipid-like material comprised in the particles.

In certain embodiments, the end groups of the polysarcosine may be functionalized with one or more molecular moieties conferring certain properties, such as positive or negative charge, or a targeting agent that will direct the particle to a particular cell type, collection of cells, or tissue.

A variety of suitable targeting agents are known in the art. Non-limiting examples of targeting agents include a peptide, a protein, an enzyme, a nucleic acid, a fatty acid, a hormone, an antibody, a carbohydrate, mono-, oligo- or polysaccharides, a peptidoglycan, a glycopeptide, or the like. For example, any of a number of different materials that bind to antigens on the surfaces of target cells can be employed. Antibodies to target cell surface antigens will generally exhibit the necessary specificity for the target. In addition to antibodies, suitable immunoreactive fragments can also be employed, such as the Fab, Fab', F(ab')2 or scFv fragments or single-domain antibodies (e.g. camelids $V_HH$ fragments). Many antibody fragments suitable for use in forming the targeting mechanism are already available in the art.

Similarly, ligands for any receptors on the surface of the target cells can suitably be employed as targeting agent. These include any small molecule or biomolecule, natural or synthetic, which binds specifically to a cell surface receptor, protein or glycoprotein found at the surface of the desired target cell.

In certain embodiments, the polysarcosine comprises between 2 and 200, between 2 and 190, between 2 and 180, between 2 and 170, between 2 and 160, between 2 and 150, between 2 and 140, between 2 and 130, between 2 and 120, between 2 and 110, between 2 and 100, between 2 and 90, between 2 and 80, between 2 and 70, between 5 and 200, between 5 and 190, between 5 and 180, between 5 and 170, between 5 and 160, between 5 and 150, between 5 and 140, between 5 and 130, between 5 and 120, between 5 and 110, between 5 and 100, between 5 and 90, between 5 and 80, between 5 and 70, between 10 and 200, between 10 and 190, between 10 and 180, between 10 and 170, between 10 and 160, between 10 and 150, between 10 and 140, between 10 and 130, between 10 and 120, between 10 and 110, between 10 and 100, between 10 and 90, between 10 and 80, or between 10 and 70 sarcosine units.

In certain embodiments, the polysarcosine comprises the following general formula (I):

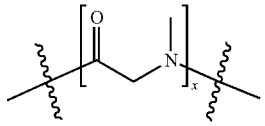

wherein x refers to the number of sarcosine units. The polysarcosine through one of the bonds may be linked to a particle-forming component or a hydrophobic component. The polysarcosine through the other bond may be linked to H, a hydrophilic group, an ionizable group, or to a linker to a functional moiety such as a targeting moiety.

Cationic Lipid

In one embodiment, the RNA-lipid particles described herein include at least one cationic lipid. As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl chain, a diacyl or more acyl chains, and the head group of the lipid typically carries the positive charge. In certain embodiments, a cationic lipid has a net positive charge only at certain pH, in particular acidic pH, while it has preferably no net positive charge, preferably has no charge, i.e., it is neutral, at a different, preferably higher pH such as physiological pH. For purposes of the present disclosure, such "cationically ionizable" lipids are comprised by the term "cationic lipid" unless contradicted by the circumstances. Examples of cationic lipids include, but are not limited to N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-1-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis(tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis(dodecyloxy)-1-propanaminium bromide (GAP-DLRIE), (1)-N-(3-aminopropyl)-N,N-dimethyl-2,3-bis(tetradecyloxy)-1-propanaminium bromide (GAP-DMRIE), N-(2-Aminoethyl)-N,N-dimethyl-2,3-bis(tetradecyloxy)-1-propanaminium bromide (PAE-DMRIE), N-(4-carboxybenzyl)-N,N-dimethyl-2,3-bis(oleoyloxy)propan-1-aminium (DOBAQ), 2-({8-[(3)-cholest-5-en-3-yloxy]octyl}oxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl)amino]butylcarboxamido)ethyl]-3,4-di[oleyloxy]-benzamide (MVL5), 1,2-dioleoyl-sn-glycero-3-ethylphosphocholine (DOEPC), 2,3-bis(dodecyloxy)-N-(2-hydroxyethyl)-N,N-dimethylpropan-1-ammonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl) dioctanoate (ATX), N,N-dimethyl-2,3-bis(dodecyloxy) propan-1-amine (DLDMA), N,N-dimethyl-2,3-bis(tetradecyloxy)propan-1-amine (DMDMA), Di((Z)-non-2-en-1-yl)-9-((4-(dimethylaminobutanoyl)oxy) heptadecanedioate (L319), N-Dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethylamino)propionamide (lipidoid 98N$_{12}$-5), 1-[2-[bis(2-hydroxydodecyl)amino] ethyl-[2-[4-[2-[bis(2 hydroxydodecyl)amino]ethyl]piperazin-1-yl]ethyl]amino]dodecan-2-ol (lipidoid C12-200).

Preferred are DODMA, DOTMA, DOTAP, DODAC, and DOSPA. In specific embodiments, the at least one cationic lipid is DODMA.

In some embodiments, the cationic lipid may comprise from about 10 mol % to about 80 mol %, from about 20 mol % to about 60 mol %, from about 25 mol % to about 55 mol %, from about 30 mol % to about 50 mol %, from about 35 mol % to about 45 mol %, or about 40 mol % of the total lipid present in the particle.

Additional Lipids

In addition to a cationic lipid, the RNA particles described herein may include one or more additional lipids. An additional lipid may be incorporated which may or may not affect the overall charge of the RNA particles. In certain embodiments, the additional lipid is a non-cationic lipid. The non-cationic lipid may comprise, e.g., one or more anionic lipids and/or neutral lipids. As used herein, a "neutral lipid" refers to any of a number of lipid species that exist either in an uncharged or neutral zwitterionic form at a selected pH. In preferred embodiments, the additional lipid comprises one of the following neutral lipid components: (1) a phospholipid, (2) cholesterol or a derivative thereof; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoyl-phosphatidylethanolamine (DMPE), dilauroyl-phosphatidylethanolamine (DLPE), diphytanoyl-phosphatidylethanolamine (DPyPE), and further phosphatidylethanolamine lipids with different hydrophobic chains.

In certain preferred embodiments, the additional lipid is DSPC or DSPC and cholesterol.

In certain embodiments, the RNA particles include both a cationic lipid and an additional lipid. In an exemplary embodiment, the cationic lipid is DODMA and the additional lipid is DSPC or DSPC and cholesterol.

Without wishing to be bound by theory, the amount of the at least one cationic lipid compared to the amount of the at least one additional lipid may affect important RNA particle characteristics, such as charge, particle size, stability, tissue selectivity, and bioactivity of the RNA. Accordingly, in some embodiments, the molar ratio of the at least one cationic lipid to the at least one additional lipid is from about 10:0 to about 1:9, about 4:1 to about 1:2, or about 3:1 to about 1:1.

In some embodiments, the non-cationic lipid, in particular neutral lipid, (e.g., one or more phospholipids and/or cholesterol) may comprise from about 0 mol % to about 90 mol %, from about 20 mol % to about 80 mol %, from about 25 mol % to about 75 mol %, from about 30 mol % to about 70 mol %, from about 35 mol % to about 65 mol %, or from about 40 mol % to about 60 mol %, of the total lipid present in the particle.

In certain preferred embodiments, the non-cationic lipid, in particular neutral lipid, comprises a phospholipid such as DSPC of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle.

In certain preferred embodiments, the non-cationic lipid, in particular neutral lipid, comprises cholesterol or a derivative thereof of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle.

In certain preferred embodiments, the non-cationic lipid, in particular neutral lipid, comprises a mixture of: (i) a phospholipid such as DSPC of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle; and (ii) cholesterol or a derivative thereof such as cholesterol of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle. As a non-limiting example, a lipid particle comprising a mixture of a phospholipid and cholesterol may comprise DSPC of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle and cholesterol of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle.

Polysarcosine-Lipid Conjugate

The RNA particles described herein such as the RNA particles described above comprising a cationic lipid and an additional lipid further include a polysarcosine conjugate such as a polysarcosine-lipid conjugate. The polysarcosine may be conjugated, in particular covalently bound to or linked to, any particle forming component such as a lipid or lipid-like material. The polysarcosine-lipid conjugate is a molecule wherein polysarcosine is conjugated to a lipid as described herein such as a cationic lipid or cationically ionizable lipid or an additional lipid. Alternatively, polysarcosine is conjugated to a lipid or lipid-like material which is different from a cationic or cationically ionizable lipid or an additional lipid.

In certain embodiments, the polysarcosine-lipid conjugate or a conjugate of polysarcosine and a lipid-like material comprises the following general formula (II):

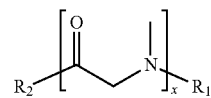

wherein one of $R_1$ and $R_2$ comprises a hydrophobic group and the other is H, a hydrophilic group, an ionizable group or a functional group optionally comprising a targeting moiety. In one embodiment, the hydrophobic group comprises a linear or branched alkyl group or aryl group, preferably comprising from 10 to 50, 10 to 40, or 12 to 20 carbon atoms. In one embodiment, $R_1$ or $R_2$ which comprises a hydrophobic group comprises a moiety such as a heteroatom, in particular N, linked to one or more linear or branched alkyl groups.

In certain embodiments, a polysarcosine-lipid conjugate or a conjugate of polysarcosine and a lipid-like material comprises the following general formula (III):

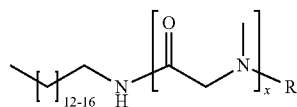

wherein R is H, a hydrophilic group, an ionizable group or a functional group optionally comprising a targeting moiety.

The symbol "x" in the general formulas herein, e.g., the general formulas (II) and (III), refers to the number of sarcosine units and may be a number as defined herein.

In certain embodiments, the polysarcosine-lipid conjugate or a conjugate of polysarcosine and a lipid-like material is a member selected from the group consisting of a polysarcosine-diacylglycerol conjugate, a polysarcosine-dialkyloxypropyl conjugate, a polysarcosine-phospholipid conjugate, a polysarcosine-ceramide conjugate, and a mixture thereof.

In certain instances, the polysarcosine-lipid conjugate may comprise from about 0.2 mol % to about 50 mol %, from about 0.25 mol % to about 30 mol %, from about 0.5 mol % to about 25 mol %, from about 0.75 mol % to about 25 mol %, from about 1 mol % to about 25 mol %, from about 1 mol % to about 20 mol %, from about 1 mol % to about 15 mol %, from about 1 mol % to about 10 mol %, from about 1 mol % to about 5 mol %, from about 1.5 mol % to about 25 mol %, from about 1.5 mol % to about 20 mol %, from about 1.5 mol % to about 15 mol %, from about 1.5 mol % to about 10 mol %, from about 1.5 mol % to about 5 mol %, from about 2 mol % to about 25 mol %, from about 2 mol % to about 20 mol %, from about 2 mol % to about 15 mol %, from about 2 mol % to about 10 mol %, or from about 2 mol % to about 5 mol % of the total lipid present in the particle.

Typically, the polysarcosine moiety has between 2 and 200, between 5 and 200, between 5 and 190, between 5 and 180, between 5 and 170, between 5 and 160, between 5 and 150, between 5 and 140, between 5 and 130, between 5 and 120, between 5 and 110, between 5 and 100, between 5 and 90, between 5 and 80, between 10 and 200, between 10 and 190, between 10 and 180, between 10 and 170, between 10 and 160, between 10 and 150, between 10 and 140, between 10 and 130, between 10 and 120, between 10 and 110, between 10 and 100, between 10 and 90, or between 10 and 80 sarcosine units.

RNA-Lipid Particles

A "RNA-lipid particle" includes a lipid formulation that can be used to deliver RNA to a target site of interest (e.g., cell, tissue, organ, and the like). A RNA-lipid particle is typically formed from a cationic lipid such as DODMA, one or more non-cationic lipids such as phospholipids (e.g., DSPC), cholesterol or analogues thereof, and a polysarcosine-lipid conjugate.

Without intending to be bound by any theory, it is believed that the cationic lipid and the additional lipids combine together with the RNA to form aggregates, wherein the nucleic acid is bound to the lipid matrix, and this spontaneous aggregation results in colloidally stable particles.

In some embodiments, RNA-lipid particles comprise more than one type of RNA molecules, where the molecular parameters of the RNA molecules may be similar or different from each other, like with respect to molar mass or fundamental structural elements such as molecular architecture, capping, coding regions or other features, In some embodiments, the RNA-lipid particles in addition to RNA comprise (i) a cationic lipid which may comprise from about 10 mol % to about 80 mol %, from about 20 mol % to about 60 mol %, from about 25 mol % to about 55 mol %, from about 30 mol % to about 50 mol %, from about 35 mol % to about 45 mol %, or about 40 mol % of the total lipid present in the particle, (ii) a non-cationic lipid, in particular neutral lipid, (e.g., one or more phospholipids and/or cholesterol) which may comprise from about 0 mol % to about 90 mol %, from about 20 mol % to about 80 mol %, from about 25 mol % to about 75 mol %, from about 30 mol % to about 70 mol %, from about 35 mol % to about 65 mol %, or from about 40 mol % to about 60 mol %, of the total lipid present in the particle, and (iii) a polysarcosine-lipid conjugate which may comprise from about 0.2 mol % to about 50 mol %, from about 0.25 mol % to about 30 mol %, from about 0.5 mol % to about 25 mol %, from about 0.75 mol % to about 25 mol %, from about 1 mol % to about 25 mol %, from about 1 mol % to about 20 mol %, from about 1 mol % to about 15 mol %, from about 1 mol % to about 10 mol %, from about 1 mol % to about 5 mol %, from about 1.5 mol % to about 25 mol %, from about 1.5 mol % to about 20 mol %, from about 1.5 mol % to about 15 mol %, from about 1.5 mol % to about 10 mol %, from about 1.5 mol % to about 5 mol %, from about 2 mol % to about 25 mol %, from about 2 mol % to about 20 mol %, from about 2 mol % to about 15 mol %, from about 2 mol % to about 10 mol %, or from about 2 mol % to about 5 mol % of the total lipid present in the particle.

In certain preferred embodiments, the non-cationic lipid, in particular neutral lipid, comprises a phospholipid of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle.

In certain preferred embodiments, the non-cationic lipid, in particular neutral lipid, comprises cholesterol or a derivative thereof of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle.

In certain preferred embodiments, the non-cationic lipid, in particular neutral lipid, comprises a mixture of: (i) a phospholipid such as DSPC of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle; and (ii) cholesterol or a derivative thereof such as cholesterol of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle. As a non-limiting example, a lipid particle comprising a mixture of a phospholipid and cholesterol may comprise DSPC of from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle and cholesterol of from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle.

Typically, the polysarcosine moiety has between 2 and 200, between 5 and 200, between 5 and 190, between 5 and 180, between 5 and 170, between 5 and 160, between 5 and 150, between 5 and 140, between 5 and 130, between 5 and 120, between 5 and 110, between 5 and 100, between 5 and 90, between 5 and 80, between 10 and 200, between 10 and 190, between 10 and 180, between 10 and 170, between 10 and 160, between 10 and 150, between 10 and 140, between 10 and 130, between 10 and 120, between 10 and 110, between 10 and 100, between 10 and 90, or between 10 and 80 sarcosine units.

In some embodiments, the RNA-lipid particles in addition to RNA comprise (i) DODMA which may comprise from about 10 mol % to about 80 mol %, from about 20 mol % to about 60 mol %, from about 25 mol % to about 55 mol %, from about 30 mol % to about 50 mol %, from about 35 mol % to about 45 mol %, or about 40 mol % of the total lipid present in the particle, (ii) DSPC which may comprise from about 5 mol % to about 50 mol %, from about 5 mol % to about 45 mol %, from about 5 mol % to about 40 mol %, from about 5 mol % to about 35 mol %, from about 5 mol % to about 30 mol %, from about 5 mol % to about 25 mol %, or from about 5 mol % to about 20 mol % of the total lipid present in the particle, (iii) cholesterol which may comprise from about 10 mol % to about 80 mol %, from about 10 mol % to about 70 mol %, from about 15 mol % to about 65 mol %, from about 20 mol % to about 60 mol %, from about 25 mol % to about 55 mol %, or from about 30 mol % to about 50 mol % of the total lipid present in the particle and (iv) a polysarcosine-lipid conjugate which may comprise from about 0.2 mol % to about 50 mol %, from about 0.25 mol % to about 30 mol %, from about 0.5 mol % to about 25 mol %, from about 0.75 mol % to about 25 mol %, from about 1 mol % to about 25 mol %, from about 1 mol % to about 20 mol %, from about 1 mol % to about 15 mol %, from about 1 mol % to about 10 mol %, from about 1 mol % to about 5 mol %, from about 1.5 mol % to about 25 mol %, from about 1.5 mol % to about 20 mol %, from about 1.5 mol % to about 15 mol %, from about 1.5 mol % to about 10 mol %, from about 1.5 mol % to about 5 mol %, from about 2 mol % to about 25 mol %, from about 2 mol % to about 20 mol %, from about 2 mol % to about 15 mol %, from about 2 mol % to about 10 mol %, or from about 2 mol % to about 5 mol % of the total lipid present in the particle.

In certain embodiments, the RNA particles include a polysarcosine-lipid conjugate according to the general formula (II) or (III), DODMA, DSPC and cholesterol RNA Particle Diameter RNA particles described herein have an average diameter that in one embodiment ranges from about 30 nm to about 1000 nm, from about 30 nm to about 800 nm, from about 30 nm to about 700 nm, from about 30 nm to about 600 nm, from about 30 nm to about 500 nm, from about 30 nm to about 450 nm, from about 30 nm to about 400 nm, from about 30 nm to about 350 nm, from about 30 nm to about 300 nm, from about 30 nm to about 250 nm, from about 30 nm to about 200 nm, from about 30 nm to about 190 nm, from about 30 nm to about 180 nm, from about 30 nm to about 170 nm, from about 30 nm to about 160 nm, from about 30 nm to about 150 nm, from about 50 nm to about 500 nm, from about 50 nm to about 450 nm, from about 50 nm to about 400 nm, from about 50 nm to about 350 nm, from about 50 nm to about 300 nm, from about 50 nm to about 250 nm, from about 50 nm to about 200 nm, from about 50 nm to about 190 nm, from about 50 nm to about 180 nm, from about 50 nm to about 170 nm, from about 50 nm to about 160 nm, or from about 50 nm to about 150 nm.

In certain embodiments, RNA particles described herein have an average diameter that ranges from about 40 nm to about 800 nm, from about 50 nm to about 700 nm, from about 60 nm to about 600 nm, from about 70 nm to about 500 nm, from about 80 nm to about 400 nm, from about 150 nm to about 800 nm, from about 150 nm to about 700 nm, from about 150 nm to about 600 nm, from about 200 nm to about 600 nm, from about 200 nm to about 500 nm, or from about 200 nm to about 400 mu.

RNA particles described herein, e.g. generated by the processes described herein, exhibit a polydispersity index less than about 0.5, less than about 0.4, less than about 0.3, less than about 0.2 or about 0.1 or less. By way of example, the RNA particles can exhibit a polydispersity index in a range of about 0.1 to about 0.3.

RNA

In the present disclosure, the term "RNA" relates to nucleic acid molecules which include ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA. In particular embodiments, the RNA according to the invention comprises a population of different RNA molecules, e.g. a mixture of different RNA molecules optionally encoding different peptides and/or proteins. Thus, according to the invention, the term "RNA" may include a mixture of RNA molecules. In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In certain embodiments of the present disclosure, the RNA is replicon RNA or simply "a replicon", in particular self-replicating RNA. In one particularly preferred embodiment, the replicon or self-replicating RNA is derived from or comprises elements derived from a ssRNA virus, in particular a positive-stranded ssRNA virus such as an alphavirus. Alphaviruses are typical representatives of positive-stranded RNA viruses. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In certain embodiments of the present disclosure, the RNA in the RNA particles described herein is at a concentration from about 0.002 mg/mL to about 5 mg/mL, from about 0.002 mg/mL to about 2 mg/mL, from about 0.005 mg/mL to about 2 mg/mL, from about 0.01 mg/mL to about 1 mg/mL, from about 0.05 mg/mL to about 0.5 mg/mL or from about 0.1 mg/mL to about 0.5 mg/mL. In specific embodiments, the RNA is at a concentration from about 0.005 mg/mL to about 0.1 mg/mL, from about 0.005 mg/mL to about 0.09 mg/mL, from about 0.005 mg/mL to about 0.08 mg/mL, from about 0.005 mg/mL to about 0.07 mg/mL, from about 0.005 mg/mL to about 0.06 mg/mL, or from about 0.005 mg/mL to about 0.05 mg/mL.

In one embodiment, the RNA may have modified ribonucleotides. Examples of modified ribonucleotides include, without limitation, 5-methylcytidine, pseudouridine (ψ), N1-methyl-pseudouridine ($m^1\psi$) or 5-methyl-uridine ($m^5U$).

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. The term "poly (A) sequence" relates to a sequence of adenyl (A) residues which typically is located at the 3'-end of a RNA molecule. According to the disclosure, in one embodiment, a poly(A) sequence comprises at least about 20, at least about 40, at least about 80, or at least about 100, and up to about 500, up to about 400, up to about 300, up to about 200, or up to about 150 A nucleotides, and in particular about 120 A nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

RNA can be coding RNA, i.e. RNA encoding a peptide or protein. Said RNA may express the encoded peptide or protein. For example, said RNA may be RNA encoding and expressing a pharmaceutically active peptide or protein. Alternatively, the RNA can be non-coding RNA such as antisense-RNA, micro RNA (miRNA) or siRNA.

RNA used herein may be pharmaceutically active RNA. A "pharmaceutically active RNA" is a RNA that encodes a pharmaceutically active peptide or protein or is pharmaceutically active in its own, e.g., it has one or more pharmaceutical activities such as those described for pharmaceutically active proteins, e.g., immunostimulatory activity. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

Some aspects of the disclosure involve the targeted delivery of the RNA disclosed herein to certain cells or tissues. In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding an antigen or epitope for inducing an immune response. In one embodiment, the target cell is a spleen cell. In one embodiment, the target cell is an antigen presenting cell such as a professional antigen presenting cell in the spleen. In one embodiment, the target cell is a dendritic cell in the spleen. The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naive lymphocytes and initiate an adaptive immune response.

Lipid-based RNA delivery systems have an inherent preference to the liver. Liver accumulation is caused by the discontinuous nature of the hepatic vasculature or the lipid metabolism (liposomes and lipid or cholesterol conjugates). In one embodiment, the target organ is liver and the target tissue is liver tissue. The delivery to such target tissue is preferred, in particular, if presence of RNA or of the encoded peptide or protein in this organ or tissue is desired and/or if it is desired to express large amounts of the encoded peptide or protein and/or if systemic presence of the encoded peptide or protein, in particular in significant amounts, is desired or required.

In one embodiment, after administration of the RNA particles described herein, at least a portion of the RNA is delivered to a target cell or target organ. In one embodiment, at least a portion of the RNA is delivered to the cytosol of the target cell. In one embodiment, the RNA is RNA encoding a peptide or protein and the RNA is translated by the target cell to produce the peptide or protein. In one embodiment, the target cell is a cell in the liver. In one embodiment, the target cell is a muscle cell. In one embodiment, the target cell is an endothelial cell. In one embodiment the target cell is a tumor cell or a cell in the tumor microenvironment. In one embodiment, the target cell is a blood cell. In one embodiment, the target cell is a cell in the lymph nodes. In one embodiment, the target cell is a cell in the lung. In one embodiment, the target cell is a blood cell. In one embodiment, the target cell is a cell in the skin. In one embodiment, the target cell is a spleen cell. In one embodiment, the target cell is an antigen presenting cell such as a professional antigen presenting cell in the spleen. In one embodiment, the target cell is a dendritic cell in the spleen. In one embodiment, the target cell is a T cell. In one embodiment, the target cell is a B cell. In one embodiment, the target cell is a NK cell. In one embodiment, the target cell is a monocyte. Thus, RNA particles described herein may be used for delivering RNA to such target cell. Accordingly, the present disclosure also relates to a method for delivering RNA to a target cell in a subject comprising the administration of the RNA particles described herein to the subject. In one embodiment, the RNA is delivered to the cytosol of the target cell. In one embodiment, the RNA is RNA encoding a peptide or protein and the RNA is translated by the target cell to produce the peptide or protein.

In an embodiment, RNA encodes a pharmaceutically active peptide or protein.

According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g. in the cytoplasm), may secrete the encoded peptide or protein, or may produce it on the surface.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" refers to large peptides, in particular peptides having at least about 151 amino acids, but the terms "peptide" and "protein" are used herein usually as synonyms.

A "pharmaceutically active peptide or protein" or "therapeutic peptide or protein" has a positive or advantageous effect on a condition or disease state of a subject when provided to the subject in a therapeutically effective amount. In one embodiment, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein.

Examples of pharmaceutically active proteins include, but are not limited to, cytokines and derivatives thereof such as cytokine-fusions (like albumin-cytokine fusions) and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, chimeric antigen receptors (CARs), immunoglobulins including antibodies or bispecific antibodies, e.g., for immune stimulation or production of neutralizing antibodies in case of viral/bacterial infection, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases, lysosomal enzymes and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

The term "immunologically active compound" relates to any compound altering an immune response, for example, by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases. Immunologically active compounds can be useful as vaccine adjuvants.

In one embodiment, a pharmaceutically active peptide or protein comprises a cytokine. The term "cytokine" refers to a category of small proteins (~5-20 kDa) that are important in cell signalling. Their release has an effect on the behavior of cells around them. Cytokines are involved in autocrine signalling, paracrine signalling and endocrine signalling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

In one embodiment, a pharmaceutically active peptide or protein comprises a replacement protein. In this embodiment, the present invention provides a method for treatment of a subject having a disorder requiring protein replacement (e.g., protein deficiency disorders) comprising administering to the subject RNA as described herein encoding a replacement protein. The term "protein replacement" refers to the introduction of a protein (including functional variants thereof) into a subject having a deficiency in such protein. The term also refers to the introduction of a protein into a subject otherwise requiring or benefiting from providing a protein, e.g., suffering from protein insufficiency. The term "disorder characterized by a protein deficiency" refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults.

In one embodiment, a pharmaceutically active peptide or protein comprises one or more antigens or one or more epitopes, i.e., administration of the peptide or protein to a subject elicits an immune response against the one or more antigens or one or more epitopes in a subject which may be therapeutic or partially or fully protective.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a processing product thereof such as a T cell epitope is in one embodiment bound by a T or B cell receptor, or by an immunoglobulin molecule such as an antibody. Accordingly, an antigen or a processing product thereof may react specifically with antibodies or T-lymphocytes (T-cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted, in particular when presented on the surface of antigen presenting cells or diseased cells such as cancer cells in the context of MHC molecules and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured. In certain embodiments of the present disclosure, the RNA encodes at least one epitope.

In certain embodiments, the epitope is derived from a tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope"), RNA that encodes at least ten epitopes (termed a "decatope"), RNA that encodes at least twenty epitopes (termed a "eicosatope").

Compositions Comprising RNA Particles

The term "plurality of RNA particles" or "plurality of RNA-lipid particles" refers to a population of a certain number of particles. In certain embodiments, the term refers to a population of more than 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, $10^{21}$, $10^{22}$, or $10^{23}$ or more particles.

It will be apparent to those of skill in the art that the plurality of particles can include any fraction of the foregoing ranges or any range therein.

In embodiments, the composition of the present disclosure is a liquid or a solid. Non-limiting examples of a solid include a frozen form, a lyophilized form or a spray-dried form. In a preferred embodiment, the composition is a liquid.

According to the present disclosure, the compositions described herein may comprise salts such as organic or inorganic salts, including, but not limited to, sodium chloride, potassium chloride, dipotassium phosphate, monopotassium phosphate, potassium acetate, potassium bicarbonate, potassium sulfate, potassium acetate, disodium phosphate, monosodium phosphate, sodium acetate, sodium bicarbonate, sodium sulfate, sodium acetate, lithium chloride, magnesium chloride, magnesium phosphate, calcium chloride, and sodium salts of ethylenediaminetetraacetic acid (EDTA) and amino acids.

Compositions described herein may also comprise a stabilizer to avoid substantial loss of the product quality and, in particular, substantial loss of RNA activity during storage, freezing, lyophilization and/or spray-drying, for example to reduce or prevent aggregation, particle collapse, RNA degradation and/or other types of damage.

In an embodiment, the stabilizer is a cryoprotectant or lyoprotectant.

In an embodiment the stabilizer is a carbohydrate. The term "carbohydrate", as used herein refers to and encompasses monosaccharides, disaccharides, trisaccharides, oligosaccharides and polysaccharides.

In an embodiment, the stabilizer is an amino acid or a surfactant (e.g. poloxamer).

According to the present disclosure, the RNA particle compositions described herein have a pH suitable for the stability of the RNA particles and, in particular, for the stability of the RNA. In one embodiment, the RNA particle compositions described herein have a pH from about 4.0 to about 8.0, or about 5.0 to about 7.5. Without wishing to be bound by theory, the use of buffer maintains the pH of the composition during manufacturing, storage and use of the composition. In certain embodiments of the present disclosure, the buffer may be sodium bicarbonate, monosodium phosphate, disodium phosphate, monopotassium phosphate, dipotassium phosphate, [tris(hydroxymethyl)methylamino] propanesulfonic acid (TAPS), 2-(Bis(2-hydroxyethyl) amino)acetic acid (Bicine), 2-Amino-2-(hydroxymethyl) propane-1,3-diol (Tris), N-(2-Hydroxy-1,1-bis (hydroxymethyl)ethyl)glycine (Tricine), 3-[[1,3-dihydroxy-2-(hydroxymethyl)propan-2-yl]amino]-2-hydroxypropane-1-sulfonic acid (TAPSO), 2-[4-(2-hydroxyethyl)piperazin-1-yl]ethanesulfonic acid (HEPES), 2-[[1,3-dihydroxy-2-(hydroxymethyl)propan-2-yl]amino]ethanesulfonic acid (TES), 1,4-piperazinediethanesulfonic acid (PIPES), dimethylarsinic acid, 2-morpholin-4-ylethanesulfonic acid (MES), 3-morpholino-2-hydroxypropanesulfonic acid (MOPSO), or phosphate buffered saline (PBS). Other suitable buffering systems may be acetic acid alone or in a salt, citric acid alone or in a salt, boric acid alone or in a salt and phosphoric acid alone or in a salt, or amino acids and amino acid derivatives.

Certain embodiments of the present disclosure contemplate the use of a chelating agent in a composition described herein. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation in the present disclosure. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid (DTPA), bis(aminoethyl)glycolether-N,N,N',N'-tetraacetic acid, iminodiacetic acid, citric acid, tartaric acid, fumaric acid, or a salt thereof. In certain embodiments, the chelating agent is EDTA or a salt of EDTA. In an exemplary embodiment, the chelating agent is EDTA disodium dihydrate.

In some embodiments, the EDTA is at a concentration from about 0.05 mM to about 5 mM, from about 0.1 mM to about 2.5 mM or from about 0.25 mM to about 1 mM.

Pharmaceutical Compositions

The compositions comprising RNA particles described herein are useful as or for preparing pharmaceutical compositions or medicaments for therapeutic or prophylactic treatments.

In one aspect, RNA particles described herein are present in a pharmaceutical composition. In another aspect, a composition described herein is a pharmaceutical composition.

The particles of the present disclosure may be administered in the form of any suitable pharmaceutical composition.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises RNA particles as described herein.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cyctokines, such as monokines, lymphokines, interleukins, chemokines. The chemokines may be IL-1, IL-2, IL-3, IL-4, IL-5, IL-6, IL-7, IL-8, IL-9, IL-10, IL-12, INFa, INF-γ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys, as well as lipophilic components, such as saponins, trehalose-6,6-dibehenate (TDB), monophosphoryl lipid-A (MPL), monomycoloyl glycerol (MMG), or glucopyranosyl lipid adjuvant (GLA).

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the particles or compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the particles or compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions

In one embodiment, pharmaceutical compositions described herein may be administered intravenously, intraarterially, subcutaneously, intradermally, dermally, intramuscularly or intratumorally. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration.

Use of Pharmaceutical Compositions

RNA particles described herein may be used in the therapeutic or prophylactic treatment of various diseases, in particular diseases in which provision of a peptide or protein to a subject results in a therapeutic or prophylactic effect. For example, provision of an antigen or epitope which is derived from a virus may be useful in the treatment of a viral disease caused by said virus. Provision of a tumor antigen or epitope may be useful in the treatment of a cancer disease wherein cancer cells express said tumor antigen. Provision of a functional protein or enzyme may be useful in the treatment of genetic disorder characterized by a dysfunctional protein, for example in lysosomal storage diseases (e.g. Mucopolysaccharidoses) or factor deficiencies. Provision of a cytokine or a cytokine-fusion may be useful to modulate tumor microenvironment.

The term "disease" (also referred to as "disorder" herein) refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate), or any other non-mammal-animal, including birds (chicken), fish or any other animal species that can be afflicted with or is susceptible to a disease or disorder (e.g., cancer, infectious diseases) but may or may not have the disease or disorder, or may have a need for prophylactic intervention such as vaccination, or may have a need for interventions such as by protein replacement. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide protection against an infectious disease by vaccination.

In one embodiment of the disclosure, the aim is to provide secreted therapeutic proteins, such as antibodies, bispecific antibodies, cytokines, cytokine fusion proteins, enzymes, to a subject, in particular a subject in need thereof.

In one embodiment of the disclosure, the aim is to provide a protein replacement therapy, such as production of erythropoietin, Factor VII, Von Willebrand factor, β-galactosidase, Alpha-N-acetylglucosaminidase, to a subject, in particular a subject in need thereof.

In one embodiment of the disclosure, the aim is to modulate/reprogram immune cells in the blood.

A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

The terms "immunization" or "vaccination" describe the process of administering an antigen to an individual with the purpose of inducing an immune response, for example, for therapeutic or prophylactic reasons.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Materials and Methods

Materials mRNA that encodes for luciferase, or secreted NanoLuc® luciferase (secNLuc), was provided by the RNA Biochemistry unit (BioNTech RNA Pharmaceuticals, Mainz, Germany) (mRNA concentration is between 2 and 5 mg/mL in water or 10 mM Hepes; 0.1 mM EDTA; pH 7.0). The ionizable cationic lipid DODMA (1,2-dioleyloxy-N,N-dimethyl-3-aminopropane) and the helper lipid DOPE (1,2-dioleoyl-sn-glycero-3-phosphoethanolamine) were purchased from Merck. The helper lipid DSPC (1,2-distearoyl-sn-glycero-3-phosphocholine) was obtained from Avanti Polar Lipids. Cholesterol was from Sigma Aldrich. Sodium dodecyl sulfate (SDS) was obtained from Sigma Adlrich.

Prior to preparation, lipids are dissolved in absolute ethanol (Carl Roth) to a concentration between 5 and 100 mM and the ethanolic lipid solutions are stored at −20° C.

Prior to preparation, ethanolic lipid solution, sterile citrate buffer 100 mM pH 5.4 and RNA were equilibrated at room temperature.

Protocol 1 for Preparation of Lipid Nanoparticles

Lipid nanoparticles were prepared by mixing an ethanol phase containing the lipids with an aqueous phase containing the RNA using a microfluidic mixing device, the Nano-Assemblr™ Benchtop Instrument (Precision NanoSystems, Vancouver, BC). One volume of ethanol containing the lipid mixture at 9 mM total lipid and 3 volumes of RNA at 0.15 mg/mL in citrate buffer 100 mM pH 5.4, were mixed through the microfluidic cartridge at a combined flow rate of 12 mL/min. The resultant mixture was directly mixed with 2 volumes of citrate buffer 100 mM, pH 5.4. If not mentioned otherwise, the particles were dialyzed against phosphate buffered saline (PBS) for 2.5 h in a 10K MWCO dialysis cassette (Slide-A-Lyser, ThermoFisher Scientific). The particles were then re-concentrated by ultrafiltration using Amicon® Ultra Centrifugal filters (30 kDa NMWL, Merck Millipore) to a theoretical RNA concentration of about 0.2 to 0.5 mg/mL. The physicochemical characterization (size, polydispersity, zeta potential, RNA accessibility and total RNA concentration) was performed on the day of preparation. After complete characterization, formulations were stored at 4° C. for not more than 2 days. Lipid nanoparticles were dissolved in PBS to the desired RNA concentration prior to in vitro testing or in vivo injection.

Protocol 2 for Preparation of Lipid Nanoparticles

Lipid nanoparticles were prepared by mixing an aqueous phase containing the lipids with an aqueous phase containing the RNA. pSarc-Liposomes were prepared by ethanol injection of 600 μl at 75 mM of total lipid, containing a cationic lipid, helper lipids with or without pSarc, at different molar fractions, into a total volume of 14.4 ml of water under stirring for 30 min. Then liposomes were added to RNA in water at N/P 4 followed by rapidly vortex forming pSarc-LPX with final RNA concentration of 0.05 mg/ml. The physicochemical characterization (size, polydispersity, RNA accessibility and total RNA concentration) was performed on the day of preparation. After complete characterization, formulations were stored at 4° C. for not more than 2 days. Lipid nanoparticles were dissolved in water to the desired RNA concentration prior to in vitro testing.

Particle Size Measurement

The particle size and polydispersity (PDI) of the lipid nanoparticles were measured by dynamic light scattering. The formulations were diluted in PBS to a final RNA concentration of 0.005 mg/mL. 120 μL of diluted sample were measure in triplicate in a 96-well plate. The sizes were measured by DynaPro plate reader II instrument from WYATT technology GmbH (Dernbach, Germany).

Measurement of Zeta Potential (Electrophoretic Mobility)

The RNA lipid nanoparticles were diluted to an RNA concentration of 0.01 mg/mL in PBS 0.1× in 1 ml. Three samples of 1.05 ml were prepared for each formulation in plastic cuvettes. The electrophoretic mobility of the particles was measured by laser dopler electrophoresis with the ζ-Wallis instrument (Corduan technologies, France). Medium resolution measurement with 1 sequence of 10 runs was used for each sample. Measurement with low signal to noise ratios, or with extreme mobility μ (>3 or <−3 μm*cm/V*S) were excluded from the final analysis.

RiboGreen Assay for RNA Accessibility and Total RNA Concentration

RNA lipid nanoparticles were always concentrated at a final concentration of about 0.2 to 0.5 mg/mL RNA. The Quant-iT RiboGreen RNA assay (Thermo Fischer Scientific) was used to quantify the RNA accessibility as well as the total RNA concentration in the formulation. Briefly, the encapsulation efficiency was determined using the RNA binding dye RiboGreen by comparing fluorescence between samples in the presence and absence of 2% Triton X-100. In the absence of detergent, fluorescence can be measured from accessible free RNA only, whereas in the presence of detergent, fluorescence is measured from the total RNA amount. The fluorescence of samples in the presence of the detergent Triton X-100 was also used to calculate the total RNA concentration based on a calibration curve.

Lipid nanoparticle samples or PBS (negative control) were diluted with 1×TE buffer (Thermo Fisher Scientist) down to a mRNA concentration between 2 and 5 μg/mL.

Aliquots of each diluted samples was further diluted 1:1 in 1×TE buffer (measuring accessible mRNA) or 1:1 in 1×TE buffer containing 2% Triton-X100 (measuring total mRNA, both accessible within the particle and free mRNA). Samples were prepared in duplicate. Samples were incubated 10 min at 37° C. to ensure sufficient lipid dissociation. Quant-iT RiboGreen RNA reagent (1:100 dilutions from the stock solution in TE buffer) was then added 1.1 to each sample and the fluorescence of the dye was measured at an excitation wavelength of 485 nm and emission 535 nm (Tecan Infinite M200 Pro Multimode Plate Reader).

The RNA accessibility was determined as follows:

$$RNA\ Accessibility\ \% = \left[\left(\frac{free\ RNA}{total\ RNA}\right)\right] \times 100$$

The total RNA concentration was determined using an RNA calibration curve in 1×TE buffer with 2% Triton X-100.

Agarose Gel Electrophoresis

Agarose gel electrophoresis was performed to evaluate free RNA. The gel was poured by using 1 g agarose dissolved in 100 mL of 1×TAE Buffer (Tris-acetate-EDTA) (ThermoFisher), 1 mL of 5% Sodium hypochlorite, and 10 μL of GelRed Nucleic Acid Gel Stain (Biotium). The gel was allowed to set for at least 25 min at room temperature. The gel was then placed in a gel electrophoresis tank and 1×TAE running buffer (ThermoFisher) was used. Before loading, the samples were incubated at 40° C. with or without 2% of Triton X-100, for total and free RNA, respectively. The gel was run at 80 V for 40 minutes. Gel images were taken on a Chemidoc XRS imaging system (Bio-Rad).

In-Vitro Transfection Assay and Cell Viability Assay

Cells were seeded in white 96-well plate (flat bottom) at concentration of 5000 cells per well for C2C12 cells, at 20 000 cells per well for HepG2 and TC1 cells. The cells were maintained at 37° C. and 5% CO2, except C2C12 at 7.5% C02. After 18-24 h, the supernatant was discarded and replaced with 90 µL of respective mediums supplemented with 10% of non-inactivated FCS. Formulations were diluted to a final concentration of 1 to 10 µg/mL in PBS. Then 10 µl of the lipid nanoparticle solution was added to the cells to obtain a final medium volume of 100 µl. The final RNA quantity in the wells ranges from 33 to 100 ng. Plates were centrifugated 5 min at 500 g at room temperature. After 24 h incubation with the cells, Bright-Glo™ Luciferase assay (Cat. #E260, Promega GmbH, Mannheim, Germany) was performed according to manual instructions. Bioluminescence signals (RLU) were measured using a Tecan Infinite M200 Pro Multimode Plate Reader and luciferase expression was calculated by subtracting the background of non-transfected cells (using PBS as a blank).

For cell viability measurement, the same procedure was followed. After 24 h incubation of formulation with the cells, CellTiter-Glo™ assay (Cat. G9242, Promega GmbH, Mannheim, Germany) was performed according to manual instructions. Controls with PBS for 100% viability and DMSO for toxicity were included. Viability was calculated as follows:

$$\text{Viability \%} = \left[\frac{RLU\,sample - RLU\,blank}{RLU\,PBS - RLU\,blank}\right] \times 100$$

In-Vivo Transfection in Mice

Mice are anaesthetized with isoflurane and 200 µl of the investigated formulations at 0.05 mg/mL luciferase coding mRNA were injected intravenously into to retro-orbital sinus with an insulin-syringe pre-equipped with a cannula of 30G in size. The mouse was observed until regaining consciousness for signs of pain, suffering and distress.

At the time of measurement (6 h and 24 h post dose), mice were injected intraperitoneally with D-Luciferin-solution at 100 mg/kg body weight. Subsequently, mice were anesthetized with Isoflurane and placed on a heat mat (37° C.) inside the IVIS® Spectrum (Perkin Elmer) imaging chamber with constant supply of Isoflurane/oxygen via individual anesthesia masks.

Five minutes after injection of luciferin, detection of bioluminescence light over one minute via camera was performed. Mice were then sacrificed by cervical elongation, organs like liver, lung, spleen, heart, kidney, brain, lymph nodes were collected and measured again ex-vivo with the IVIS® Spectrum imaging device. Resulting images were analyzed using the software "LivingImage" (Perkin Elmer). Region of interest (ROI) were drawn around the organs to quantify the total flux of photon [p/s]. Blood was drawn, and the serum was obtained by centrifugation of the whole blood at 1000×g for 3 min. Liver enzyme levels of alanine aminotransferase (ALT), aspartate aminotransferase (AST), and LDH levels were determined by Thermo scientific clinical chemistry analyzer-Indiko.

For EPO experiments, Balb/c mice (n=5) were intravenously administrated with an mRNA dose range from 30 to 3 µg. Whole blood was drawn after 3, 6, 24 and 48 h and plasma was obtained by centrifugation at 13000×rpm for 3 min. EPO secretion was determined using Mouse Erythropoietin DuoSet ELISA (R&D systems).

Small Angle X-Rays Scattering

Small Angle X-Ray Scattering (SAXS) experiments were conducted on the German Synchrotron—EMBL (DESY) Hamburg [P12]. The sample to detector distance was adjustable between 1.6 and 6 m to allow measurements from q=0.6 Å-1 to q=3 Å-1. Concentrated LNP suspensions were loaded on site into quartz capillary tubes using a syringe.

Complement Activation

In vitro C3a levels were determined using Human C3a EIA kit (Quidel). Briefly, LNPs and controls (positive (Cremophore El) and negative (1×PBS and EDTA (18 mM)) were incubated with Normal Human Serum Complement (NHS, Quidel) at a ratio of 20:80 (Specimen:NHS) for 1 h at 37° C. LNPs were tested at 5×, 1× and 0.02× based on a theoretical plasma concentration of 1 mg/kg mRNA dose. C3a EIA kit was performed according manufactures protocol.

Cryo-TEM

Samples were preserved in vitrified ice supported by holey carbon films on 200-mesh copper grids (QuantiFoil® R2/1). Vitrification was performed in liquid ethane at −180° C. with a Leica EM GP. Grids were stored under liquid Nitrogen until transferred to the electron microscope for imaging. Cryogenic TEM imaging was performed with Zeiss Libra® 120 under liquid N2 cryo conditions on holey carbon-coated copper grids. The microscope was used at 120 kV acceleration voltage and the images were acquired with a Gatan UltraScan® ccd camera. Images of each grid were acquired at multiple scales to assess the overall distribution of the specimen.

Example 2: Generation of RNA Lipid Nanoparticles Comprising a pSarc mRNA lipid nanoparticles were prepared using an amino acid based polypeptide lipid: polysarcosine-conjugated lipids.

LNPs were prepared by mixing an ethanol phase containing the lipids DODMA, Cholesterol, DSPC and C14pSarc20 at 40:50-X:10:X molar ratio and 3 volumes of RNA at 0.15 mg/mL in citrate buffer 100 mM pH 5.4.

TABLE 1

Physicochemical characterization of RNA lipid nanoparticles prepared with different molar fraction (%) of C14pSarc20.

| Composition | Ratio | N/P | Z-Av (nm) | PdI | RNA Accessibility (%) |
|---|---|---|---|---|---|
| DODMA:Chol:DSPC:C14PSARC20 | 40:49.5:10:0.5 | 2.7 | — | — | 51.2 |
| DODMA:Chol:DSPC:C14PSARC20 | 40:49:10:1 | 2.7 | — | — | 72.5 |
| DODMA:Chol:DSPC:C14PSARC20 | 40:48.5:10:2.5 | 2.7 | 222.8 | 0.159 | 74.2 |
| DODMA:Chol:DSPC:C14PSARC20 | 40:45:10:5 | 2.7 | 117.8 | 0.177 | 52.3 |

TABLE 1-continued

Physicochemical characterization of RNA lipid nanoparticles
prepared with different molar fraction (%) of C14pSarc20.

| Composition | Ratio | N/P | Z-Av (nm) | PdI | RNA Accessibility (%) |
|---|---|---|---|---|---|
| DODMA:Chol:DSPC:C14PSARC20 | 40:42.5:10:7.5 | 2.7 | 129.4 | 0.195 | 75.9 |
| DODMA:Chol:DSPC:C14PSARC20 | 40:40:10:10 | 2.7 | 81 | 0.193 | 68.3 |
| DODMA:Chol:DSPC:C14PSARC20 | 40:35:10:15 | 2.7 | 63.1 | 0.173 | 62.0 |
| DODMA:Chol:DSPC:C14PSARC20 | 40:30:10:20 | 2.7 | 57.3 | 0.238 | 72.2 |

FIG. 1 shows the relationship between the particle size and the molar fraction of pSarcosylated LNPs. Lipid nanoparticles were manufactured using lipid mixtures comprising increasing molar fractions of C14PSarc20. Under suitable conditions, colloidally stable particles can be obtained. While with very low fractions of PSarc (0.5 and 1%) no particles of measurable size were formed, at 2.5 mol % and above particles with discrete size and low polydispersity index were obtained. The particle size could be accurately fine-tuned by variation of the PSarc fraction. Particle size decreased monotonously from about 200-250 nm with 2.5 mol % of PSarc to about 50 nm with 20 mol % of PSarc.

Example 3: Particles with pSarc-Lipids with Different Sarcosine Polymerization Unit Length LNPs were prepared by mixing one volume of an ethanol phase containing the lipids DODMA, Cholesterol, DSPC and C14pSarcX with different polymer length (X=11, 20, 34 or 65) at 40:45:10:5 molar ratio and 3 volumes of RNA at 0.15 mg/mL in citrate buffer 100 mM pH 5.4.

TABLE 2

Physicochemical characterization of RNA lipid nanoparticles prepared with
5 molar fraction (%) of C14pSarc with different polymerization lengths.

| Composition | Ratio | N/P | Z-Av (nm) | PdI | Zeta potential | RNA Accessibility % | Free RNA (%) |
|---|---|---|---|---|---|---|---|
| DODMA:Chol:DSPC:C14PSARC11 | 40:45:10:5 | 2.7 | 106.8 | 0.317 | 2.09 ± 1.43 | 72.5 | 1.6 |
| DODMA:Chol:DSPC:C14PSARC20 | 40:45:10:5 | 2.7 | 107.5 | 0.174 | 2.6 ± 0.7 | 75.9 | 5.1 |
| DODMA:Chol:DSPC:C14PSARC34 | 40:45:10:5 | 2.7 | 83.4 | 0.202 | 2.04 ± 1.82 | 72.2 | 16.8 |
| DODMA:Chol:DSPC:C14PSARC65 | 40:45:10:5 | 2.7 | 114.7 | 0.237 | 1.15 ± 2.43 | 69.1 | 16.0 |

Figure 2:
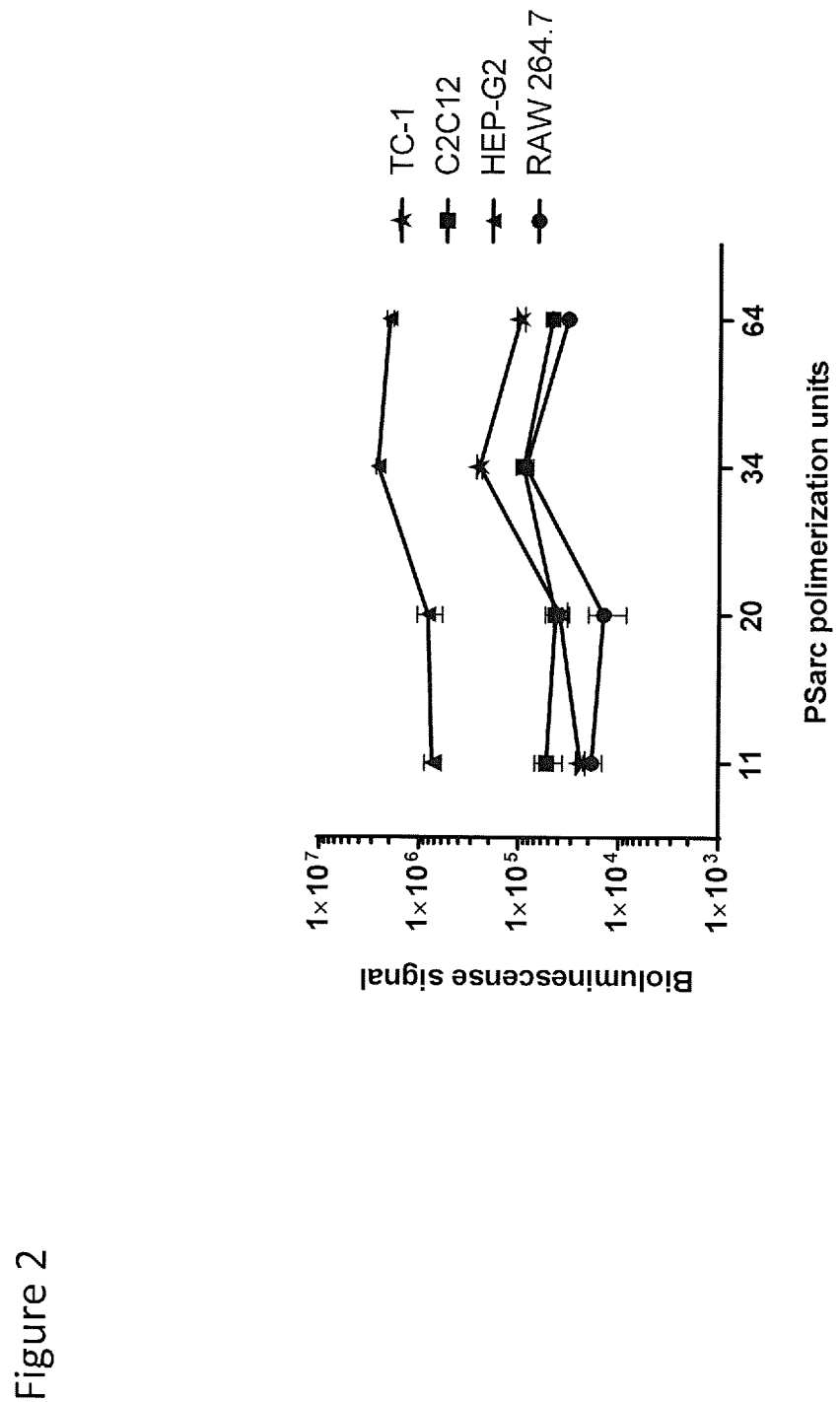
FIG. 2: Relationship between the Polysarcosine lengths (polymerization units) of PSarc lipids used for LNP formation and in-vitro protein expression of luciferase-encoding mRNA LNPs in different cell lines. LNPs formulated with mRNA encoding luciferase were tested in lung tumor cells (TC-1) muscle cells (C2C12), hepatocytes (Hep-G2) and macrophages (RAW 264.7). 24 h after transfection, bioluminescence signal was measured. Independently of the cell line, the increase of the number of polymerization units in pSarcosine did not lead to a decrease of protein expression levels as it is usually observed for PEG-lipids.

FIG. 2 shows the relationship between the Polysarcosine lengths (polymerization units) of PSarc lipids used for LNP formation and in-vitro protein expression of luciferase-encoding mRNA LNPs in different cell lines. LNPs formulated with mRNA encoding luciferase were tested in lung tumor cells (TC-1) muscle cells (C2C12), hepatocytes (HepG2) and macrophages (RAW 264.7). 24 h after transfection, bioluminescence signal was measured. Independently of the cell line, the increase of the number of polymerization units in pSarcosine did not lead to a decrease of protein expression levels as it is usually observed for PEG-lipids.

Figure 3:
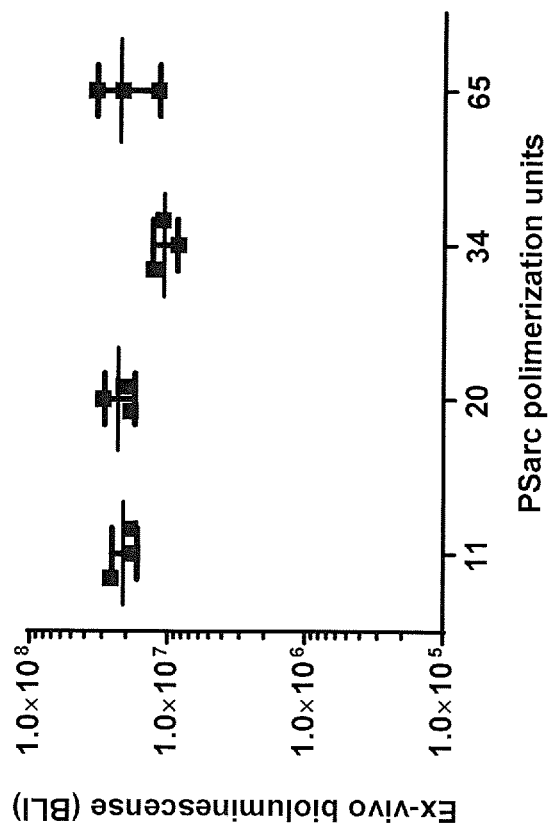
FIG. 3: In vivo efficacy of LNPs comprising constant fraction of PSarc lipid (5%), where the polysarcosine length was varied between 11 and 65 units. The LNPs formulated with mRNA encoding luciferase were injected intravenously into mice (10 μg of RNA, n=3). In vivo and ex vivo bioluminescence was measured. In all cases strongest signals were found in the liver. In the figure, data from ex vivo measurements from the livers are shown, which were extracted 6 hours after injection. No significant influence of the Polysarcosine length on the protein expression level in the liver could be determined. This allows engineering of particles using a wide range of sizes of PSarc, without reducing the transfection efficiency.

FIG. 3 shows the in vivo efficacy of LNPs comprising constant fraction of PSarc lipid (5%), where the polysarcosine length was varied between 11 and 65 units. The LNPs formulated with mRNA encoding luciferase were injected intravenously into mice (10 μg of RNA, n=3). In vivo and ex vivo bioluminescence was measured. In all cases strongest signals were found in the liver. In the figure, data from ex vivo measurements from the livers are shown, which were extracted 6 hours after injection. No significant influence of the Polysarcosine length on the protein expression level in the liver could be determined. This allows engineering of particles using a wide range of sizes of PSarc, without reducing the transfection efficiency.

Example 4: Impact of the Polysarcosine-Lipid End Group

LNPs were prepared by mixing one volume of an ethanol phase containing the lipids DODMA, Cholesterol, DSPC and C14pSarc20 with different end-groups ($NH_2$, COOH, and $C_2H_3O$) at 40:50-x:10:x molar ratio and 3 volumes of RNA at 0.15 mg/mL in citrate buffer 100 mM pH 5.4.

TABLE 3

Physicochemical characterization of RNA lipid nanoparticles prepared with different molar fraction (%) of C14pSarc20 with 3 different endgroups.

| Composition | Molar ratio | N/P | Size [d · nm] | PdI | ζ [mV] | σ | Acessibility (%) | σ | Free RNA |
|---|---|---|---|---|---|---|---|---|---|
| DODMA:Chol:DSPC:C14PSARC20-NH2 | 40:47.5:10:2.5 | 2.7 | 187 | 0.325 | 10 | 1.04 | 64.9 | 3.1 | 63.7 |
| DODMA:Chol:DSPC:C14PSARC20-NH2 | 40:45:10:5 | 2.7 | 110 | 0.175 | 4.5 | 1 | 61.7 | 2.0 | 0.0 |
| DODMA:Chol:DSPC:C14PSARC20-NH2 | 40:40:10:10 | 2.7 | 95.6 | 0.201 | 1.4 | 1.13 | 72.8 | 0.2 | 14.5 |
| DODMA:Chol:DSPC:C14PSARC20-COOH | 40:47.5:10:2.5 | 2.7 | 193 | 0.131 | 6.9 | 1.73 | 56.6 | 1.6 | 0.0 |
| DODMA:Chol:DSPC:C14PSARC20-COOH | 40:45:10:5 | 2.7 | 97.1 | 0.162 | 0.7 | 1.21 | 17.4 | 0.3 | 0.0 |
| DODMA:Chol:DSPC:C14PSARC20-COOH | 40:40:10:10 | 2.7 | 69.7 | 0.199 | −2.2 | 1 | 12.9 | 0.8 | 0.0 |
| DODMA:Chol:DSPC:C14PSARC20-C2H3O | 40:47.5:10:2.5 | 2.7 | 240 | 0.141 | 2.2 | 0.76 | 57.1 | 0.4 | 0.0 |
| DODMA:Chol:DSPC:C14PSARC20-C2H3O | 40:45:10:5 | 2.7 | 139 | 0.17 | 5.2 | 0.73 | 57.4 | 1.9 | 13.5 |
| DODMA:Chol:DSPC:C14PSARC20-C2H3O | 40:40:10:10 | 2.7 | 69.3 | 0.226 | 1.1 | 1.65 | 49.3 | 1.6 | 0.0 |

Figure 4:
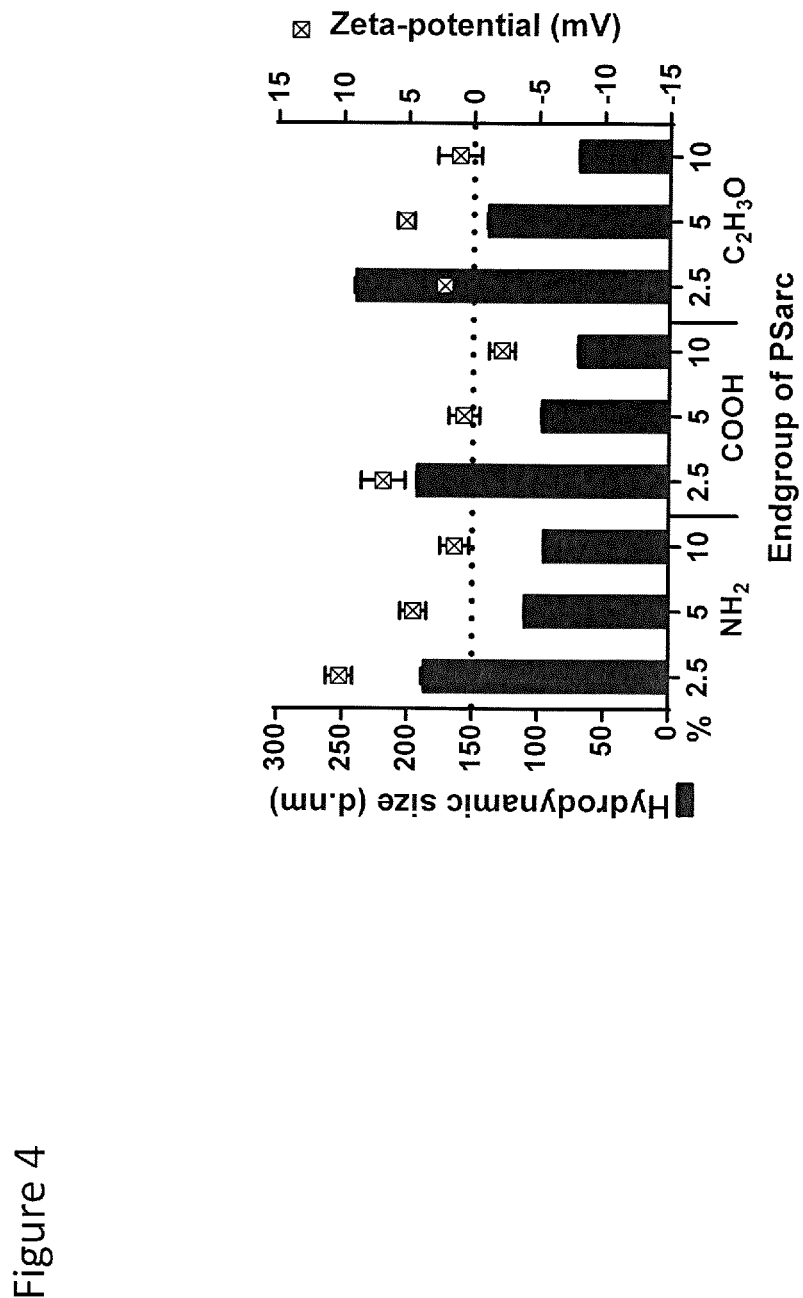

FIG. 4 shows the influence of different polysarcosine end groups on particle size and zeta potential. PSarc consisting of 20 repeat units with either an amine group, a carboxylated or an acetylated end group were tested in direct comparison. All other formulation parameters were maintained constant. Formation of LNPs with all tested end groups was successful, where the correlation between PSarc fraction and particle characteristics (size and zeta potential) was similar.

Figure 5:
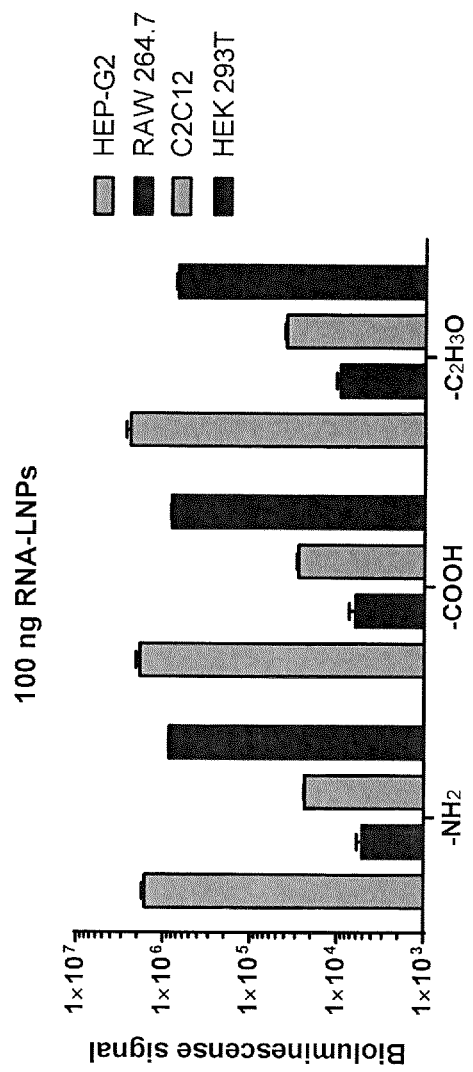
FIG. 5: In vitro characterization of LNPs comprising Polysarcosine lipids with different end groups as described in FIG. 4. PSarc lipids at a molar fraction of 5% and a length of 20 units were used. LNPs formulated with mRNA encoding luciferase were tested in hepatocytes (Hep-G2), macrophages (RAW 264.7), muscle cells (C2C12) and embryonic kidney cells (HEK 293 T). 24 h after transfection, bioluminescence signal was measured. For all LNPs and cell lines a bioluminescence signal was obtained. The dependency of signal strength as a function of cell line was similar for all end groups.

FIG. 5 shows an in vitro characterization of LNPs comprising Polysarcosine lipids with different end groups as described in FIG. 4. PSarc lipids at a molar fraction of 5% and a length of 20 units were used. LNPs formulated with mRNA encoding luciferase were tested in hepatocytes (HepG2), macrophages (RAW 264.7), muscle cells (C2C12) and embryonic kidney cells (HEK 293 T). 24 h after transfection, bioluminescence signal was measured. For all LNPs and cell lines a bioluminescence signal was obtained. The dependency of signal strength as a function of cell line was similar for all end groups.

Figure 6:
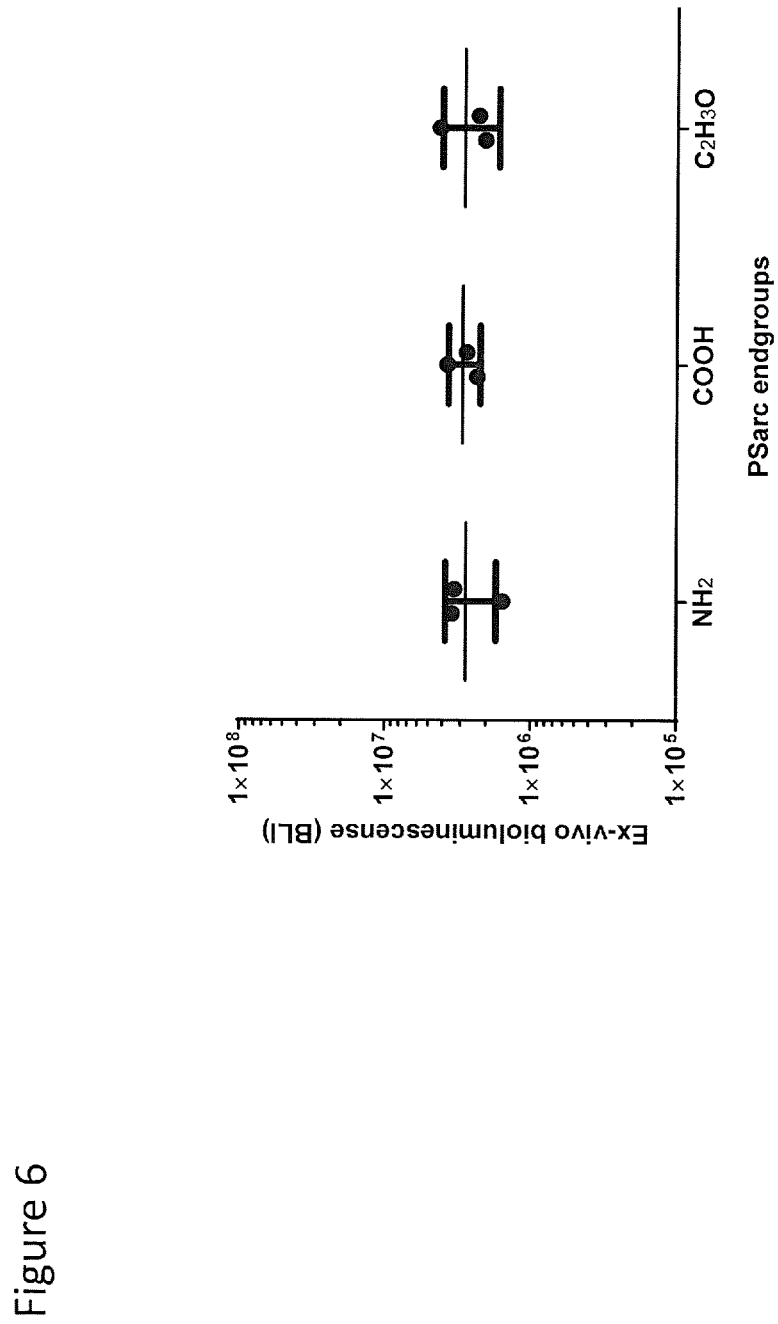
FIG. 6: In vivo efficacy of LNPs formulated with different end groups as described in FIGS. 4 and 5. PSarc lipids at a molar fraction of 5% and an a length of 20 units were used. LNPs formulated with mRNA encoding luciferase were injected intravenously (10 µg of RNA, n=3). In vivo and ex vivo bioluminescence was measured. In all cases strongest signals were found in the liver. In the figure, data from ex vivo measurements from the livers are shown, as extracted 6 hours after injection. With all end groups similar signal strengths were determined, indicating that all end groups are suitable to obtain similarly high transfection in vivo.

FIG. 6 shows the in vivo efficacy of LNPs formulated with different end groups as described in FIGS. 4 and 5. PSarc lipids at a molar fraction of 5% and an a length of 20 units were used. LNPs formulated with mRNA encoding luciferase were injected intravenously (10 μg of RNA, n=3). In vivo and ex vivo bioluminescence was measured. In all cases strongest signals were found in the liver. In the figure, data from ex vivo measurements from the livers are shown, as extracted 6 hours after injection. With all end groups similar signal strengths were determined, indicating that all end groups are suitable to obtain similarly high transfection in vivo.

Example 5: Preparation of PSarc RNA Lipid Nanoparticles with Various Cationic Lipids The results of the following experiments demonstrate the versatility of pSarcosine to form RNA lipid nanoparticles with different types of cationic moieties.

Example 6: pSarc-Liposomes and RNA-Lipoplexes

The results of the following experiments demonstrate that the inclusion of polysarcosine-conjugated lipids is suitable for formation of liposomes and stealth RNA-lipoplexes. Under appropriate conditions, small particles with high transfection efficiency are formulated. pSarc-Liposomes were prepared by injection of 600 μl of an ethanolic solution of lipids at 75 mM of total lipid, containing a cationic, helper lipids and pSarc or PEG into a total volume of 14.4 ml of water under stirring for 30 min. Then liposomes were added to RNA in water at N/P 4 followed by rapidly vortexing forming pSarc-LPX.

Figure 7:
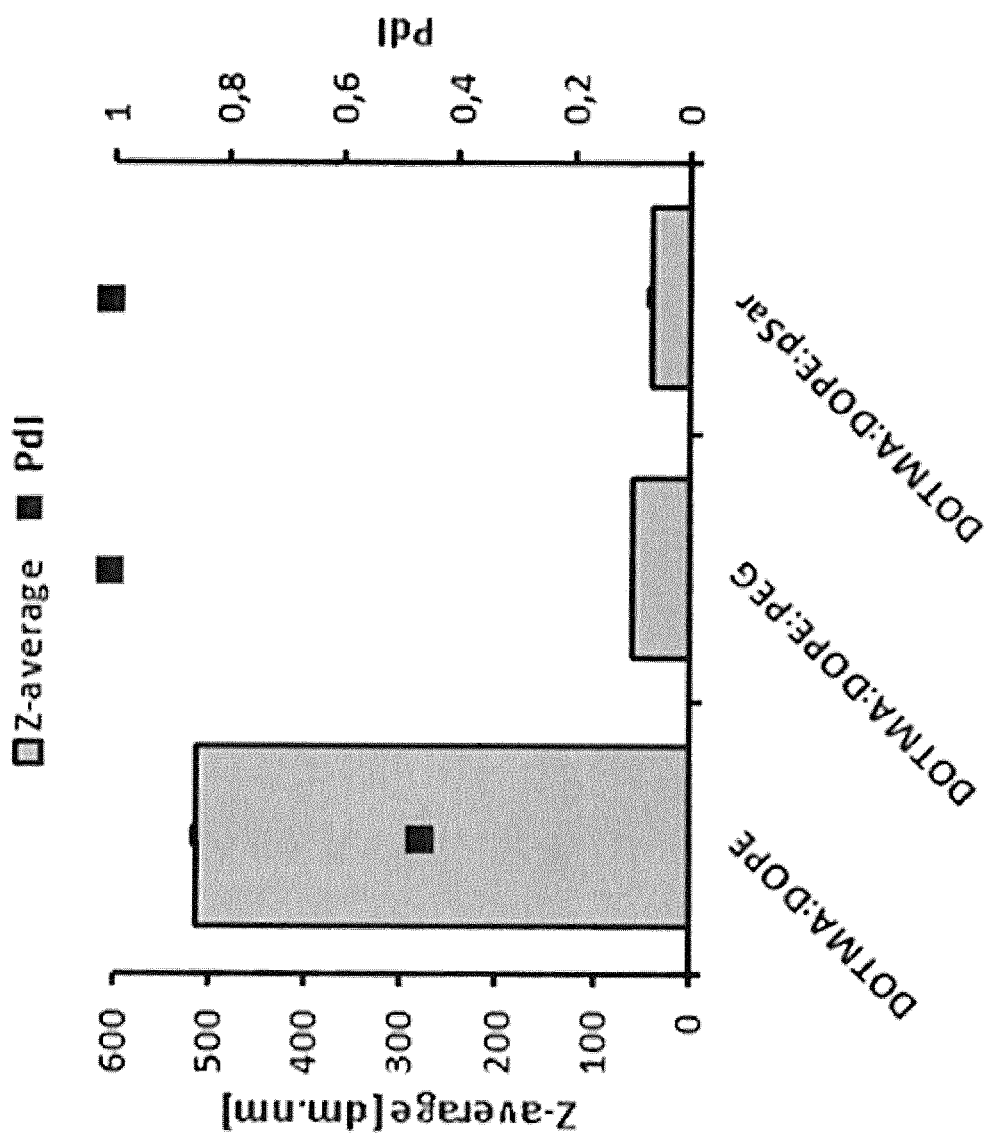
FIG. 7: Effect of PEGylation and pSarcosylation on liposomes size. Liposomes were prepared either with DOTMA and DOPE (2:1 mol/mol) alone, or lipid mixtures which comprised PEG-lipid or pSar at a molar fraction of 2% were used. Both, PEG and pSarc lead to significant reduction of the measured size, while, however, the polydispersity index was higher (multimodal).

FIG. 7 shows the effect of PEGylation and pSarcosylation on liposomes size. Liposomes were prepared either with DOTMA and DOPE (2:1 mol/mol) alone, or lipid mixtures which comprised PEG-lipid or pSar at a molar fraction of 2% were used. Both, PEG and pSarc lead to significant reduction of the measured size, while, however, the polydispersity index was higher (multimodal).

Figure 8:
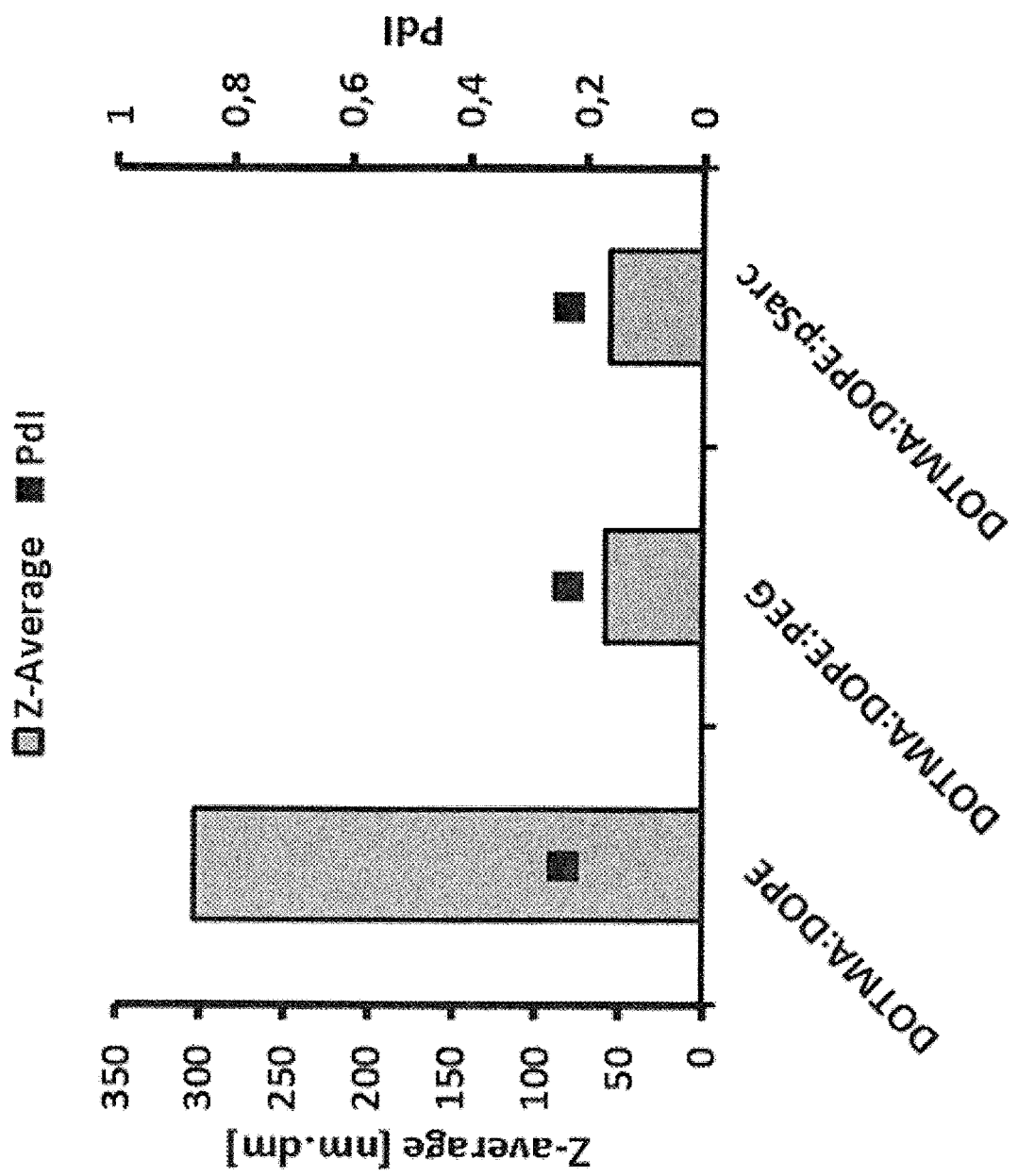
FIG. 8: Lipoplex formation using liposomes which comprise PEG and PSarc as described in FIG. 7. From all three types of liposomes (DOTMA and DOPE (2:1 mol/mol) alone, or comprising PEG-lipid or pSarc at a molar fraction of 2%), lipoplexes with confined size and low polydispersity index were formed. Lipoplexes from PEGylated and PSarcosylated liposomes showed surprisingly low polydisperisity index, in comparison to the liposome precursors where the PDI values were large. This indicates that also pSarc liposomes with high polydispersity index can be suitable for formation of well-defined RNA-lipoplexes with a rather small sizes of 50 nm and PDI of about 0.2.

FIG. 8 shows the lipoplex formation using liposomes which comprise PEG and PSarc as described in FIG. 7. From all three types of liposomes (DOTMA and DOPE (2:1 mol/mol) alone, or comprising PEG-lipid or pSarc at a molar fraction of 2%), lipoplexes with confined size and low polydispersity index were formed. Lipoplexes from PEGylated and PSarcosylated liposomes showed surprisingly low polydisperisity index, in comparison to the liposome precursors where the PDI values were large. This indicates that also pSarc liposomes with high polydispersity index can be suitable for formation of well-defined RNA-lipoplexes with a rather small sizes of 50 nm and PDI of about 0.2.

Figure 9:
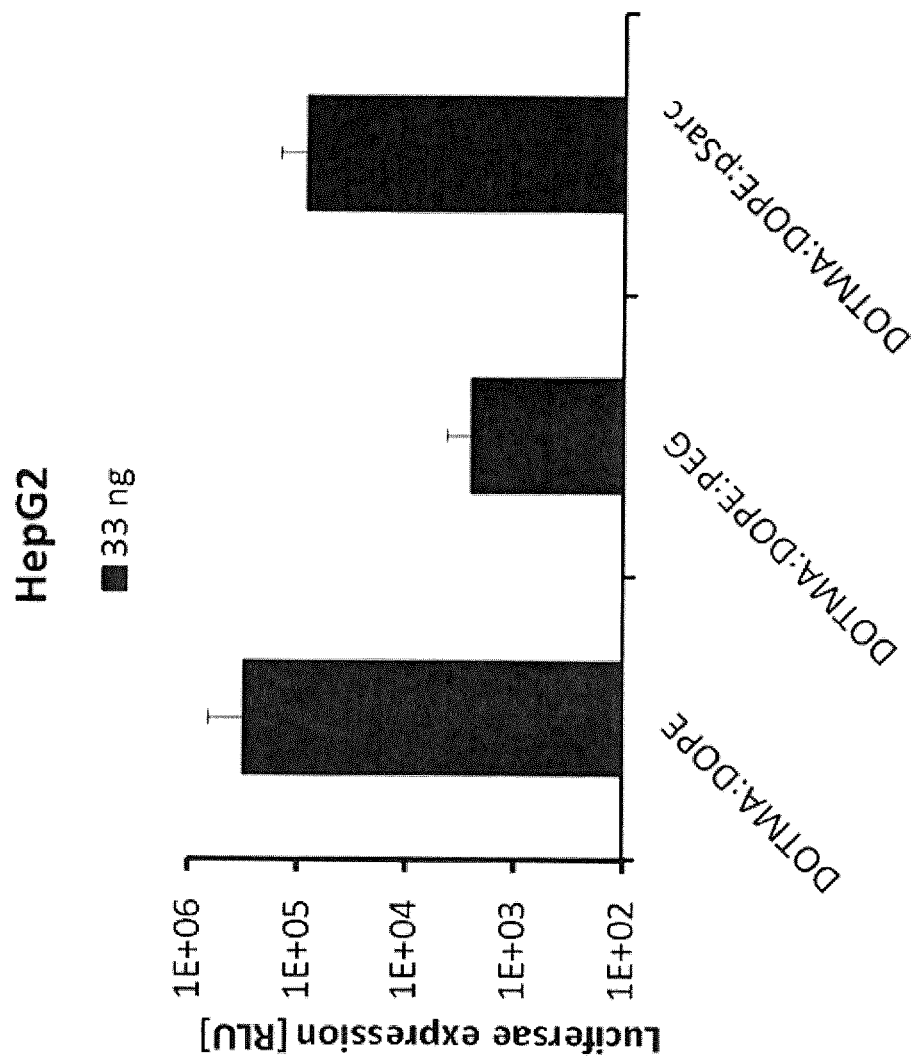
FIG. 9: In vitro characterization of lipoplexes made up from liposomes consisting of either DOTMA and DOPE (2:1 mol/mol) alone, or the same lipid mixtures comprising PEG-lipid or pSarc at a molar fraction of 2%. Lipoplexes formulated with mRNA encoding luciferase were tested in hepatocytes (Hep-G2). 24 h after transfection, bioluminescence signal was measured. While PEGylation reduced the signal significantly, this reduction was much less pronounced in case PSarc was present. PSarc appears to reduce the transfection efficacy to a much lesser extent than PEG does.

FIG. 9 described an in vitro characterization of lipoplexes made up from liposomes consisting of either DOTMA and DOPE (2:1 mol/mol) alone, or the same lipid mixtures comprising PEG-lipid or pSarc at a molar fraction of 2%. Lipoplexes formulated with mRNA encoding luciferase

TABLE 4

Physicochemical characterization of Pegylated or pSarcosylated RNA lipid nanoparticles prepared with different cationic moieties, as well as with non-conventional molar ratios of DOPE.

| Composition | Molar ratio | N/P | Size [d · nm] | PdI | ζ [mV] | σ | Accessibility (%) | σ | Free RNA |
|---|---|---|---|---|---|---|---|---|---|
| KC2:DOPE:CHOL:PEG | 40:20:38:2 | 4 | 107.2 | 0.14 | −1.17 | 1.97 | 48.4 | 2 | 8.4 |
| KC2:DOPE:CHOL:C14 pSarcC 20 | 40:20:35:5 | 4 | 0 | 0 | 1.89 | 2.17 | 4.1 | 0.2 | 0 |
| C12-200:DOPE:Chol:PEG | 40:40:18:2 | 16 | 81.55 | 0.128 | −0.44 | 2.05 | 18.8 | 0.3 | 0 |
| C12-200:DOPE:Chol:C14 pSarcC 20 | 40:40:15:5 | 16 | 155.75 | 0.234 | 6.04 | 1.36 | 3.4 | 0.2 | 0 | were tested in hepatocytes (Hep-G2). 24 h after transfection, bioluminescence signal was measured. While PEGylation reduced the signal significantly, this reduction was much less pronounced in case PSarc was present. PSarc appears to reduce the transfection efficacy to a much lesser extent than PEG does.

Figure 10:
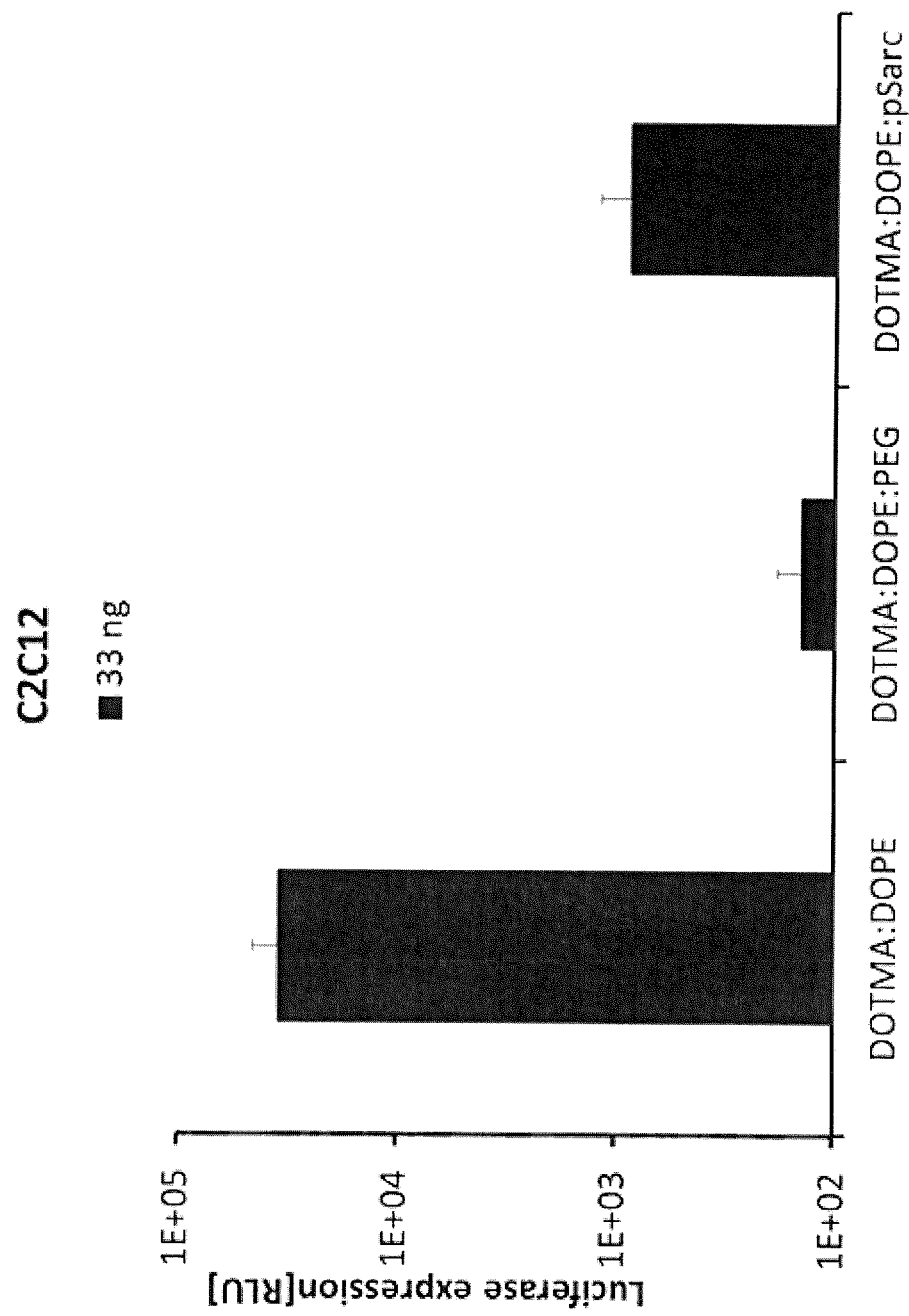
FIG. 10: In vitro characterization of lipoplexes made up from liposomes consisting of either DOTMA and DOPE (2:1 mol/mol) alone, or the same lipid mixtures comprised PEG-lipid or pSarc at a molar fraction of 2%. Lipoplexes formulated with mRNA encoding luciferase were tested in muscle cells (C2C12). 24 h after transfection, bioluminescence signal was measured. While PEGylation reduced the signal significantly, this reduction was much less pronounced in case PSarc was present. PSarc appears to reduce the transfection efficacy to a much lesser extent than PEG does.

FIG. 10 describes an in vitro characterization of lipoplexes made up from liposomes consisting of either DOTMA and DOPE (2:1 mol/mol) alone, or the same lipid mixtures comprised PEG-lipid or pSarc at a molar fraction of 2%. Lipoplexes formulated with mRNA encoding luciferase were tested in muscle cells (C2C12). 24 h after transfection, bioluminescence signal was measured. While PEGylation reduced the signal significantly, this reduction was much less pronounced in case PSarc was present. PSarc appears to reduce the transfection efficacy to a much lesser extent than PEG does.

Example 7: Further Testing of pSarc-Particles

Figure 11:
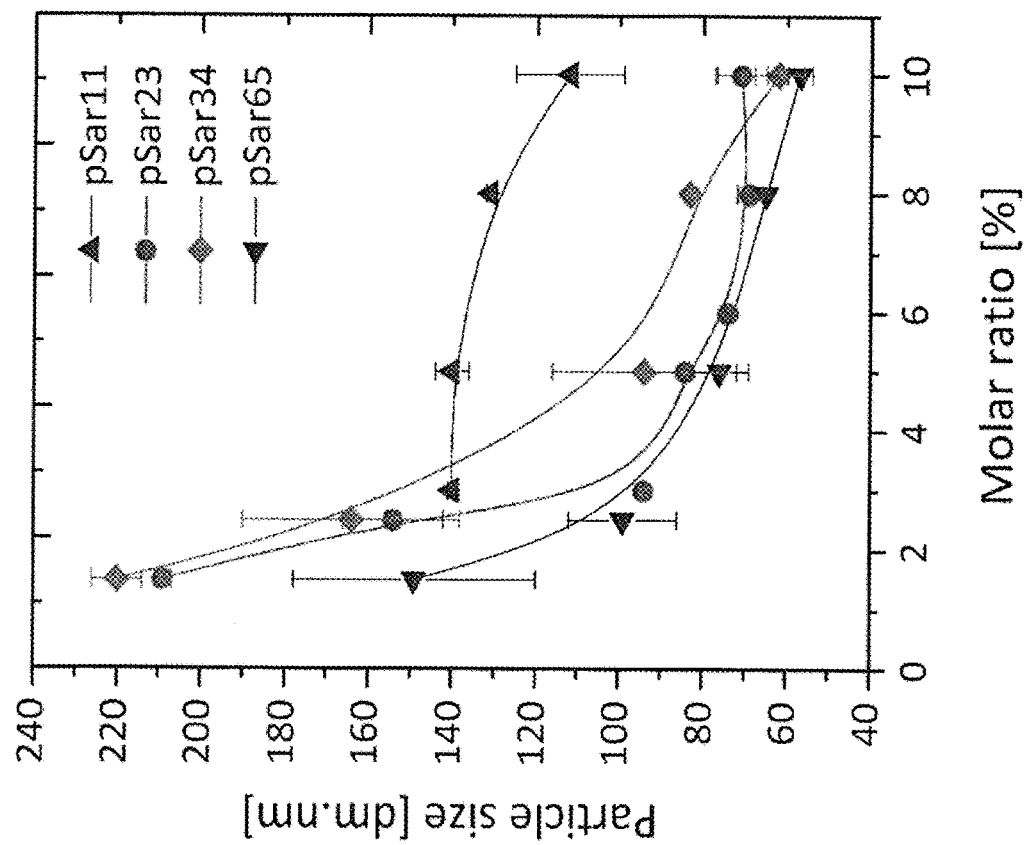
FIG. 11: Relationship between particle size and polysarcosine chain length and molar ratio in the formulation.

FIG. 11 demonstrates the relationship between particle size and polysarcosine chain length and molar ratio in the formulation. While at short polysarcosine chain length particle formation is only possible with higher molar ratio, at long polysarcosine chain length particle formation is possible at molar ratios of 1%. In general, particle size decreased with increasing polysarcosine chain length or molar ratio present in the formulation.

Figure 12:
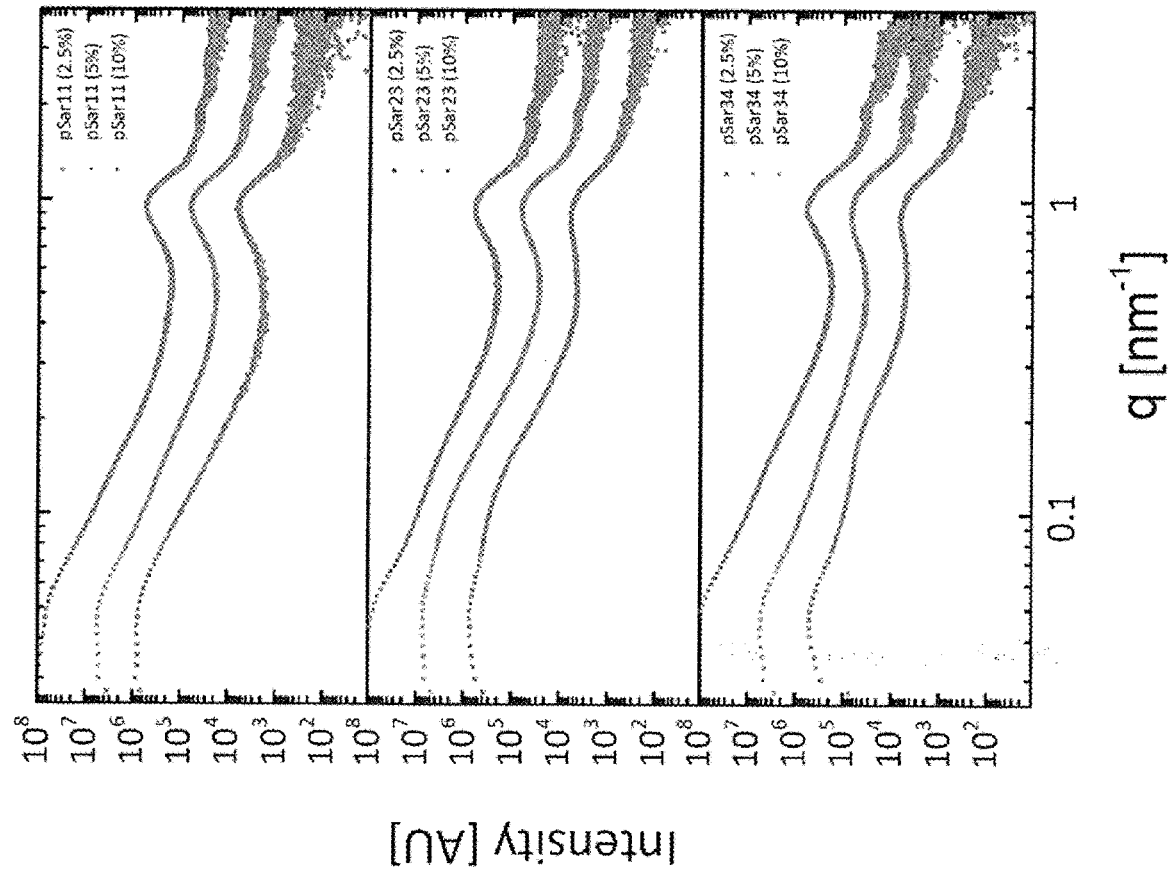
FIG. 12: Scattering curves (SAXS) from PSarcosylated lipid nanoparticles.

FIG. 12 illustrates scattering curves (SAXS) from PSarcosylated lipid nanoparticles. LNPs were formulated with polysarcosine with varying chain length (11 to 34 units) and at different molar ratios (2.5 to 10%). LNPs scattering curves demonstrate that LNPs are characterized by a low internal organization which decreased with increasing pSar chain length or molar ratio. The presence of two peaks indicates that substantial contributions are being made by the form factor of individual lipid bilayers.

Figure 13:
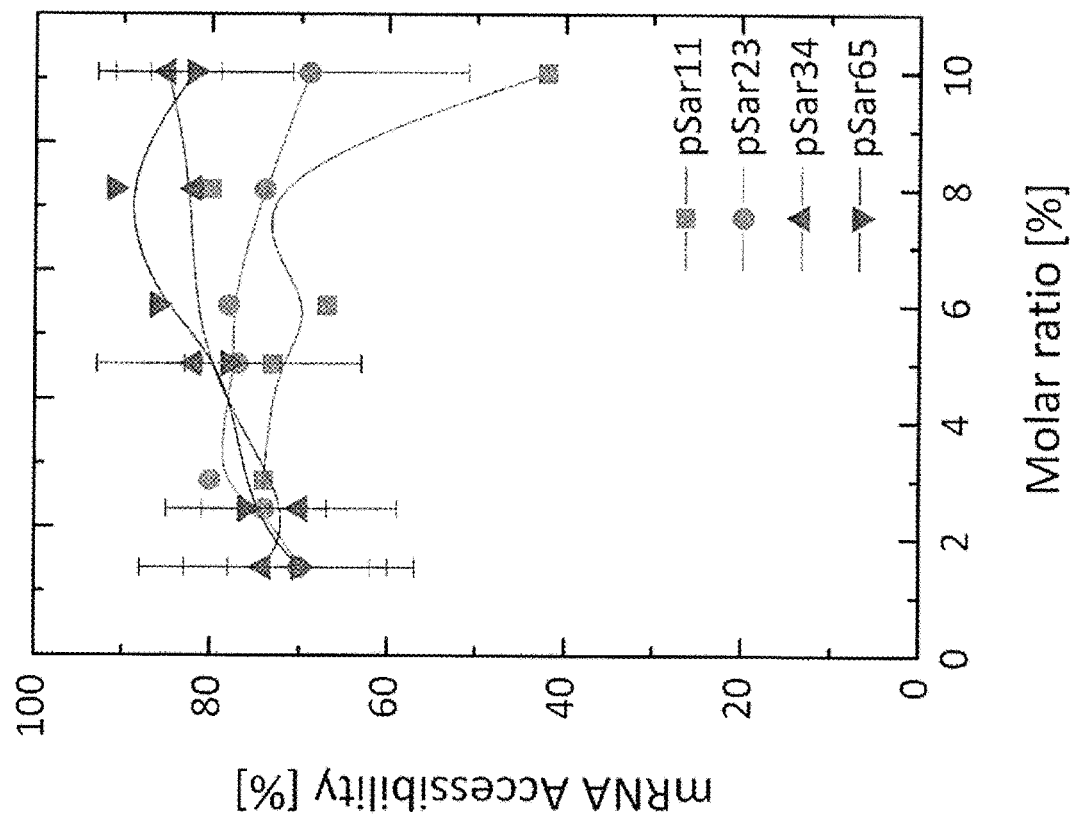
FIG. 13: RNA accessibility evaluated by Quant-It Ribogreen assay.

FIG. 13 shows the RNA accessibility evaluated by Quant-It Ribogreen assay. PSarc-LNPs show high RNA accessibility independently of polysarcosine chain length and molar ratio.

Figure 14:
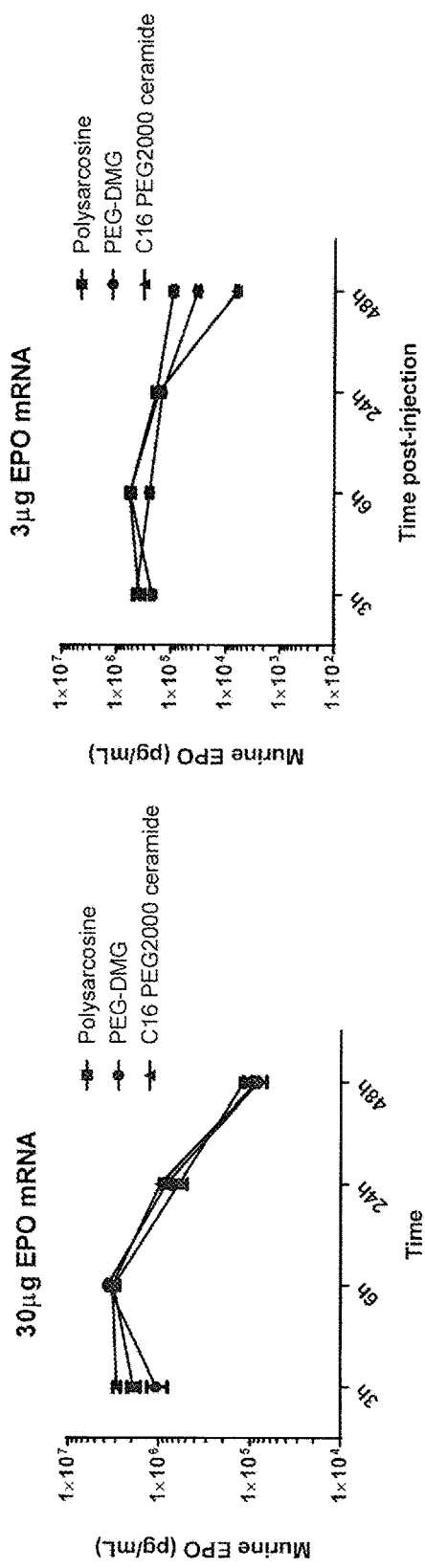
FIG. 14: Intravenous administration of varying doses of EPO (Erythropoietin)-encoding mRNA loaded into LNP formulated either with PSarc or PEG-conjugated lipids.

FIG. 14 results from intravenous administration of varying doses of EPO (Erythropoietin)-encoding mRNA loaded into LNP formulated either with PSarc or PEG-conjugated lipids. Plasma was withdraw after 3, 6, 24 and 48 h and EPO protein was quantified by ELISA. Results show that polysarcosine can directly substitute other stealth moieties like PEG-conjugated lipids without compromising the efficacy. PSarc can even promote sustained protein secretion which will be an advantage for protein replacement therapy.

Figure 15:
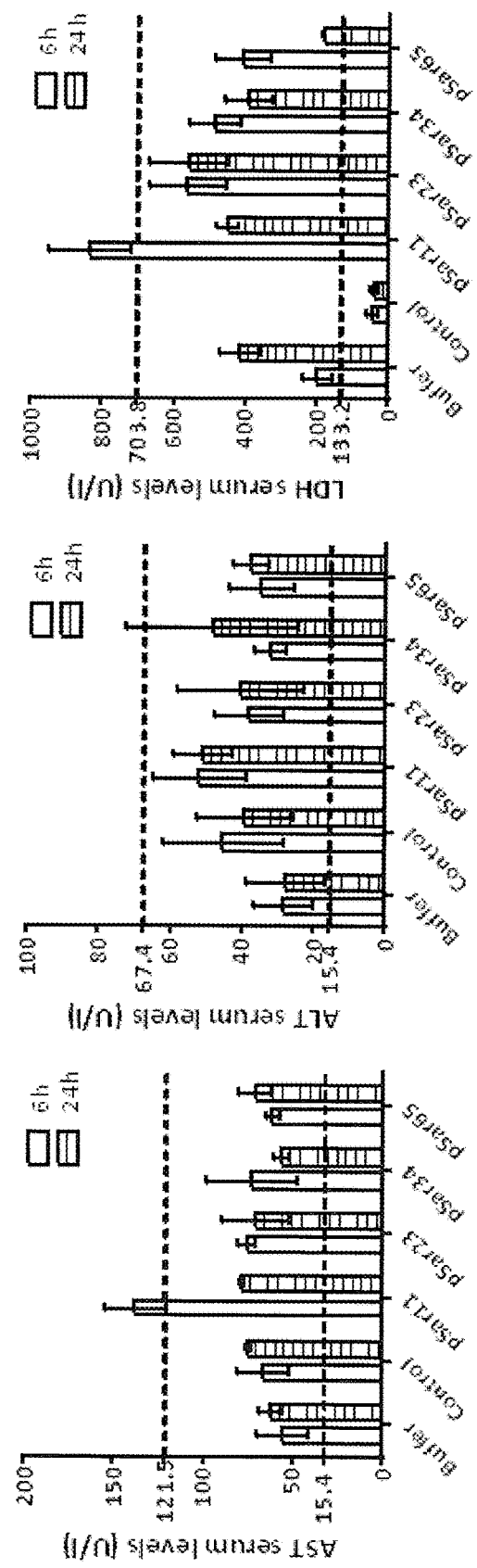
FIG. 15: Release of liver enzymes as an early marker for liver toxicity following injection of LNP formulated with increasing PSarc chain lengths.

FIG. 15 shows the release of liver enzymes as an early marker for liver toxicity. Liver enzymes as alanine aminotransferase (ALT), aspartate aminotransferase (AST) and LDH were measured in serum 6 and 24 h post injection of LNP formulated with increasing PSarc chain lengths. Data demonstrate that increasing chain lengths of PSarc did not trigger any release of liver enzymes (horizontal lines demonstrate the range of values obtained for healthy mice), demonstrating that this bio-based polymer is safe for use.

Figure 16:
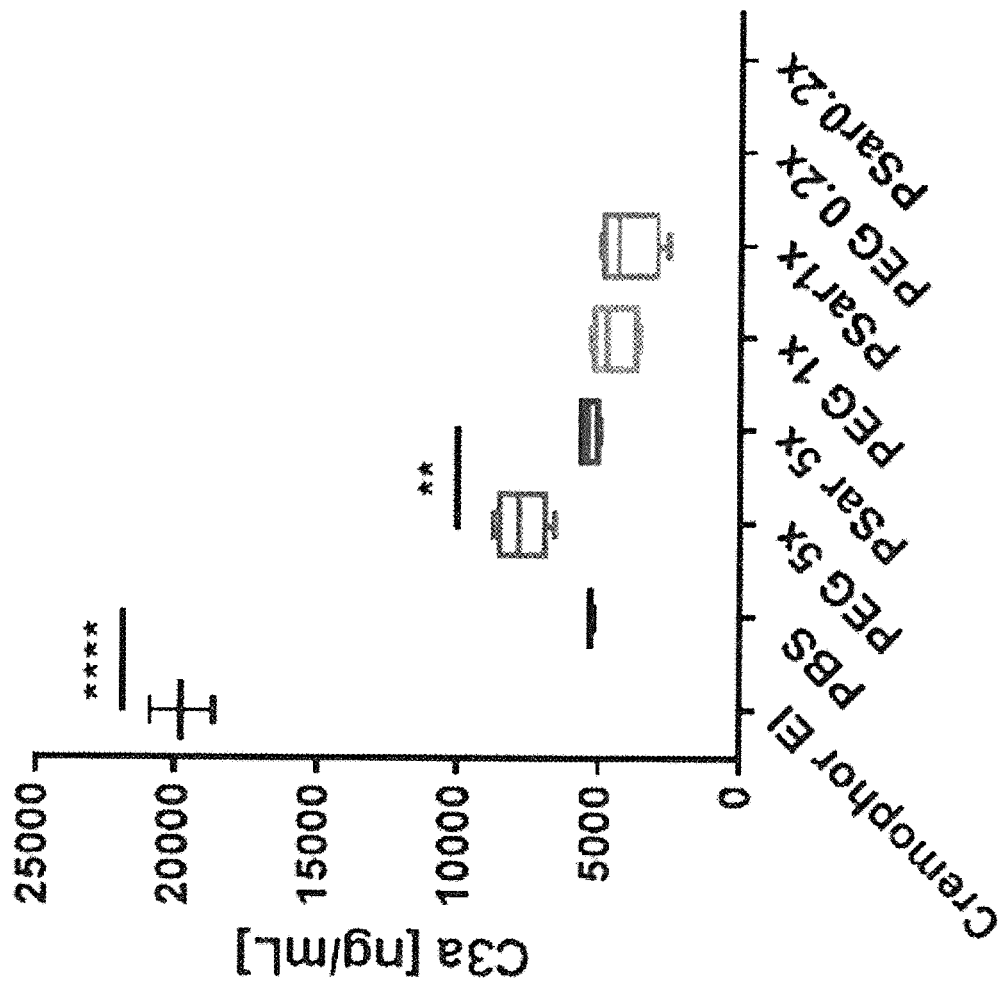
FIG. 16: Activation of complement via C3a complex of PEGylated and PSarcosylated LNP at theoretical human plasma concentration.

FIG. 16 illustrates the activation of complement via C3a complex of PEGylated and PSarcosylated LNP at theoretical human plasma concentrations. Lipid formulations and controls (positive and negative) was incubated with human serum at 20:80 ratio (sample:serum) for 1 hour at 37° C.

Data shows reduced levels of C3a complex with PSarc-LNPs when compared with PEG-LNPs at higher doses, namely five times the proposed human dose. Lower doses did not trigger the formation of C3a complex compared with PBS (formulation buffer). These results suggest that PSarc might be less immunogenic than PEG-conjugated lipids.

Figure 17:
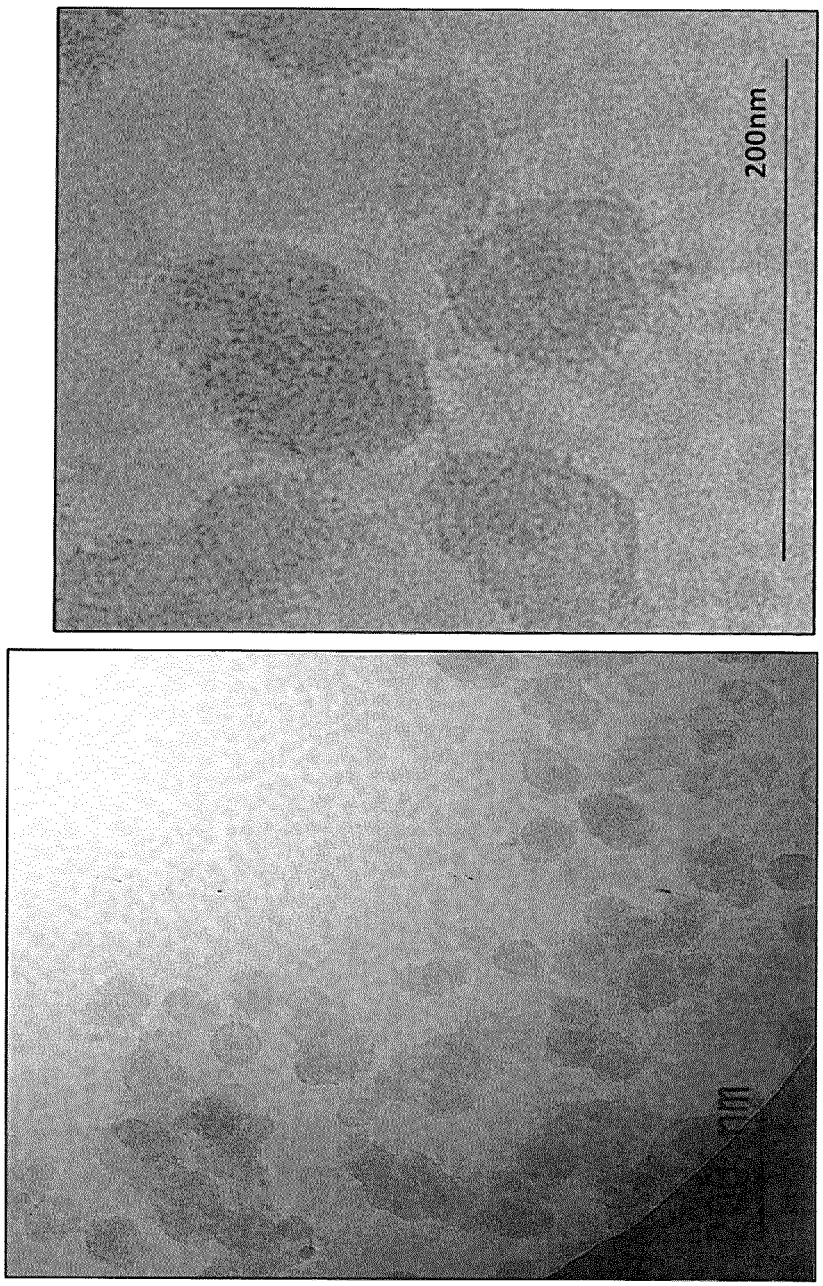
FIG. 17: Cryo-TEM image of LNP formulated with DODMA:Cholesterol:DSPC:PSarc 23 at respective mol % of 40:45:10:5. Scale bar=200 nm.

FIG. 17 shows a Cryo-TEM image of LNP formulated with DODMA:Cholesterol:DSPC:PSare 23 at respective mol % of 40:45:10:5. The morphology of polysarcosinylated LNP consist of small multilamellar vesicles where the mRNA may reside at the interface between closely apposed bilayers. Scale bar=200 nm.

In summary, the results demonstrate once more that pSarc is a versatile platform to formulate small RNA nanoparticles independently of the method, for efficient RNA delivery.

The invention claimed is:

1. A composition comprising a plurality of RNA particles, wherein each particle comprises:
    (i) RNA;
    and
    (ii) a polysarcosine-lipid conjugate comprising about 20 to 34 sarcosine units that are attached to one or more lipids which associate with RNA to form RNA liposomes or lipoplexes, wherein the one or more lipids conjugated to polysarcosine are selected from the group consisting of fatty acids, glycerolipids, glycerophospholipids, sphingolipids, saccharolipids, polyketides, sterol lipids and prenol lipids,
    wherein the polydispersity index (PDI) of the plurality of RNA particles is from 0.131 to 0.200, and wherein the Z-average particle size of the plurality of RNA nanoparticles is from 50 to 300 nm.

2. The composition of claim 1 further comprising a cationic or cationically ionizable lipid.

3. The composition of claim 2, wherein the cationically ionizable lipid is positively charged only at acidic pH and does not remain cationic at physiological pH.

4. The composition of claim 1, wherein the particles either do not comprise a polyethyleneglycol-lipid conjugate or do not comprise a conjugate of polyethyleneglycol and a lipid-like material.

5. The composition of claim 1, wherein the RNA is mRNA.

6. The composition of claim 2, wherein the cationic or cationically ionizable lipid comprises N,N-dimethyl-2,3-dioleyloxy) propylamine (DODMA), N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), N-(1-(2,3-dioleyloxy) propyl)-N,N,N-trimethylammonium chloride (DOTMA), 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-KC2-DMA), 2,2-dilinoleyl-4-dimethylaminomethyl-[1,3]-dioxolane (DLin-K-DMA), or a mixture thereof.

7. The composition of claim 1, wherein the polysarcosine-lipid conjugate is a member selected from the group consisting of a polysarcosine-diacylglycerol conjugate, a polysarcosine-dialkyloxypropyl conjugate, a polysarcosine-phospholipid conjugate, a polysarcosine-ceramide conjugate, and a mixture thereof.

8. The composition of claim 1, wherein the polysarcosine-conjugate inhibits aggregation of the particles.

9. A method for delivering RNA to cells of a subject, the method comprising administering to a subject a composition of claim 1.

10. A method for treating or preventing a disease or disorder in a subject, the method comprising administering to a subject a composition of claim 1, wherein the RNA encodes a therapeutic peptide or protein and wherein delivering the therapeutic peptide or protein to the subject is beneficial in treating or preventing the disease or disorder.

11. The method of claim 10, wherein the subject is a mammal, or wherein the mammal is a human.

* * * * *